(12) United States Patent
Croquette et al.

(10) Patent No.: US 10,196,683 B2
(45) Date of Patent: Feb. 5, 2019

(54) FORMATION OF HAIRPINS IN SITU USING FORCE-INDUCED STRAND INVASION

(71) Applicants: PARIS SCIENCES ET LETTRES—QUARTIER LATIN, Paris (FR); CENTRE NATIONAL DE LA RECHERCHE SCIENTIFIQUE (CNRS), Paris (FR); SORBONNE UNIVERSITE, Paris (FR); UNIVERSITE PARIS DIDEROT PARIS 7, Paris (FR)

(72) Inventors: Vincent Croquette, Antony (FR); Jimmy Ouellet, Paris (FR)

(73) Assignees: PARIS SCIENCES ET LETTRES—QUARTIER LATIN, Paris (FR); CENTRE NATIONAL DE LA RECHERCHE SCIENTIFIQUE (cnrs), Paris (FR); SORBONNE UNIVERSITE, Paris (FR); UNIVERSITE PARIS DIDEROT PARIS 7, Paris (FR)

( * ) Notice: Subject to any disclaimer, the term of this patent is extended or adjusted under 35 U.S.C. 154(b) by 0 days.

(21) Appl. No.: 15/570,070

(22) PCT Filed: May 4, 2016

(86) PCT No.: PCT/EP2016/060053
§ 371 (c)(1),
(2) Date: Oct. 27, 2017

(87) PCT Pub. No.: WO2016/177808
PCT Pub. Date: Nov. 10, 2016

(65) Prior Publication Data
US 2018/0105872 A1    Apr. 19, 2018

(30) Foreign Application Priority Data
May 7, 2015  (EP) .................................. 15305705

(51) Int. Cl.
*C12Q 1/68* (2018.01)
*C12Q 1/6834* (2018.01)
(Continued)

(52) U.S. Cl.
CPC ......... *C12Q 1/6834* (2013.01); *C12Q 1/6806* (2013.01); *C12Q 1/6816* (2013.01); *C12Q 1/6832* (2013.01); *C12Q 1/6874* (2013.01)

(58) Field of Classification Search
USPC ......... 435/6.1, 6.11, 91.1, 183; 436/94, 501; 536/23.1, 24.3
See application file for complete search history.

(56) References Cited

U.S. PATENT DOCUMENTS 7,556,922 B2   7/2009  Block et al.
2002/0190663 A1  12/2002  Rasmussen

FOREIGN PATENT DOCUMENTS

EP   0 146 815 A2   7/1985
EP   0 152 886 A2   8/1985
(Continued)

OTHER PUBLICATIONS

Kumar et al., Biomolecules under mechanical force, Physics Report, 486(1-2), 2010, 1-74.
(Continued)

*Primary Examiner* — Frank W Lu
(74) *Attorney, Agent, or Firm* — Arrigo, Lee, Guttmann & Mouta-Bellum LLP

(57) ABSTRACT

The present invention relates to a method of preparation of substrates for nucleic acid sequencing reactions. More specifically, the present invention provides a new method of preparing hairpins using force-induced strand invasion. Hairpins prepared by this method and methods of nucleic (Continued)

Figure 1:
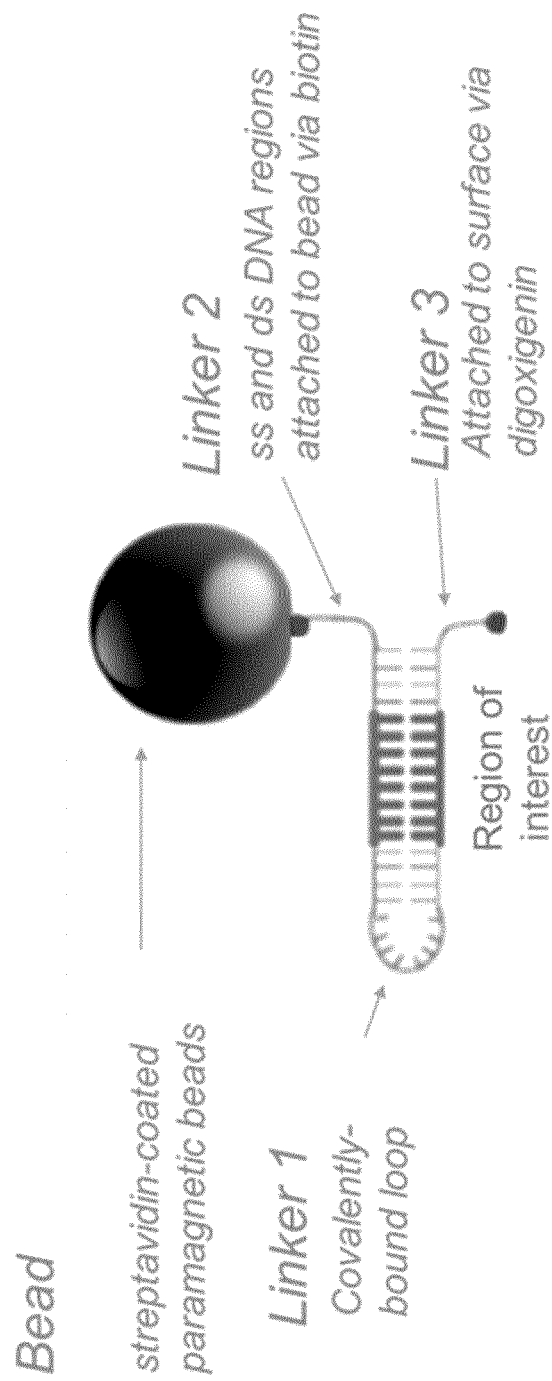

acid analysis using these hairpins are also part of the present invention.

18 Claims, 5 Drawing Sheets

Specification includes a Sequence Listing.

(51) Int. Cl.

| | | |
|---|---|---|
| *C12Q 1/6806* | (2018.01) | |
| *C12Q 1/6874* | (2018.01) | |
| *C12Q 1/6816* | (2018.01) | |
| *C12Q 1/6832* | (2018.01) | |

(56) References Cited

FOREIGN PATENT DOCUMENTS

| EP | 0 329 198 A1 | 6/1998 |
|---|---|---|
| EP | 2 390 351 A1 | 11/2011 |
| WO | 92/16659 A1 | 10/1992 |
| WO | 2011/147929 A1 | 12/2011 |
| WO | 2011/147931 A1 | 12/2011 |
| WO | 2013/093005 A1 | 6/2013 |
| WO | 2014/114687 A1 | 7/2014 |

OTHER PUBLICATIONS

Matos & West, Holliday junction resolution: Regulation in space and time, DNA Repair (Amst). 19: 176-181, 2014.

Janissen et al., Invincible DNA tethers: covalent DNA anchoring for enhanced temporal and force stability in magnetic tweezers experiments, Nucleic Acids Res. 42(18):e137, 2014.

Woodside et al., Nanomechanical measurements of the sequence-dependent folding landscapes of single nucleic acid hairpins, Proc. Natl. Acad. Sci. U.S.A., 103 (16): 6190-6195, 2006.

Greenleaf and Block, Single-Molecule, Motion-Based DNA Sequencing Using RNA Polymerase, Science, 313: 801, 2006.

European Patent Office, International Search Report in PCT/EP2016/060053, dated Jul. 20, 2016.

European Patent Office, Written Opinion of the International Searching Authority on PCT/EP2016/060053, dated Nov. 7, 2017.

FORMATION OF HAIRPINS IN SITU USING FORCE-INDUCED STRAND INVASION

The present invention relates to a method of preparation of substrates for nucleic acid sequencing reactions. More specifically, the present invention provides a new method of preparing hairpins which can be used in a single-molecule analysis process.

There are many situations when the quantity of nucleic acid (typically DNA or RNA) available to perform a genetic or epigenetic analysis is limited. Sample types include tumour biopsies, anthropology specimens, and forensic specimens. Amplification is usually performed to increase the amount of starting material. Some major disadvantages, however, are associated with amplification. In particular, the epigenetic modifications are not conserved throughout the amplification process. In addition, amplification shows variable efficiency depending on the number and sequence of the different targets being simultaneously analysed.

The inventors have previously designed a single-molecule analysis method enabling the determination of a nucleic acid sequence (WO 2011/147931; WO 2011/147929), as well as a number of related applications, including DNA detection and quantification (WO 2013/093005), and detection of protein binding to nucleic acids (WO 2014/114687). According to this method, a single nucleic acid hairpin is denatured by pulling on its extremities e.g., with magnetic tweezers. Reducing the tension below a threshold allows for the renaturation of the hairpin. However, if the said denatured hairpin has been hybridised to a single-stranded oligonucleotide, then renaturation will be blocked, at least transiently. The sequence of the double-stranded molecule can then be deciphered by determining the duration and/or location of the blockage.

This method requires the generation of hairpins which are attached at one end to a movable surface such as a bead, and at the other end to another surface. Currently, DNA hairpins are produced using classic DNA library construction techniques. Typically, such DNA hairpin structures are obtained by taking double-stranded nucleic acid molecules of interest, and attaching synthetic oligonucleotides to each end, in order to produce the required structure. This is typically performed using a DNA ligase enzyme. In addition to adding cost and time to the sample preparation, the primary disadvantage of this approach for the purposes of the sequencing method devised by the inventors is that it results in the production of a library of hairpins which must then be attached to paramagnetic beads (either during the reaction, or as a subsequent step). Furthermore, in order to interrogate the molecules using a magnetic trap instrument, the beads must ultimately be fixed via the hairpin molecule to a surface (e.g. the floor of a flow cell).

In such a scheme, it then becomes critical to adjust the molar ratio of hairpins to beads. If too many hairpins are used, the beads become densely covered with hairpins, and this can result in the attachment of the beads to the surface via multiple species of hairpins. This is a highly undesirable situation, since the single-molecule analysis method can only be performed when each bead is attached to the surface via a single hairpin, as more than one attachment point prevents the required freedom of movement during the subsequent denaturing steps. Even for beads that do become attached by one hairpin to the surface, any sample DNA which is bound elsewhere on the bead will be lost to analysis, thus squandering valuable sample material. On the other hand, if too few hairpins are used, the majority of beads will not bind to the surface at all as the probability of binding during the time which they are flowing through the flow-cell, is low.

Empirical results suggest that the optimal ratio of hairpins to beads in the protocols discussed above is somewhere between approximately 100:1 and 1000:1. While this is not a problem in situations where large quantities of the starting nucleic acids are available, in the sort of scenarios where starting material is limited, it is critical to be able to analyse a high percentage of the DNA molecules in a sample and without loss of quantitative or DNA modification information.

There is thus still a need for a method for preparing hairpins suitable for single-molecule nucleic acid analysis while maintaining quantitative accuracy.

DETAILED DESCRIPTION

The inventors have now found a new method for constructing a hairpin structure which can be used as a template for single-molecule analysis. Thus nucleic acid hairpins, suitable for subsequent analysis, can be assembled directly without the use of DNA enzymes (e.g. ligases), and in such a way that the number of DNA molecules available for analysis is maximised.

According to the method of the invention, hairpin assembly is broken into several discrete steps. The initial pre-hairpin production step is performed using synthetic DNA components and, critically, without requirement for the DNA sample of interest. It can thus be performed as a highly controlled process, in bulk, and long before the analysis itself is performed. Only the final hairpin construction requires the addition of the nucleic acid of interest.

The present invention first provides a receiving nucleic acid molecule, already bound to two distinct surfaces, which can be manufactured and quality checked in advance. This is particularly advantageous in terms of costs and time. Receiving molecules of low quality can thus be identified and discarded without wasting any precious molecules of the nucleic acid of interest, which was of course not the case with the methods of the prior art. The use of the input nucleic acid in the method of the invention is optimal, resulting in minimal sample loss and an ability to work with low-concentration samples.

According to the present invention, a nucleic acid is formed, wherein two polynucleotides are bound together through the hybridization of two complementary single-stranded regions A and A' and each of these polynucleotides is bound to a distinct surface. In addition, at least one of the two polynucleotides of this nucleic acid contains at least one stretch of single-stranded nucleic acid C. This nucleic acid is designated HP1 (for "hairpin precursor 1") and serves as a landing pad for the nucleic acid of interest. Such a structure can be formed easily and reliably, by simply allowing the two complementary single-stranded regions A and A' to hybridise.

According to the invention, the nucleic acid of interest is provided in a HP2 nucleic acid ("hairpin precursor 2"), wherein said nucleic acid of interest is a double stranded molecule bound at one end to a loop and at the other end to the same two complementary regions A and A' as in the HP1 structure. In addition, at least one of the two complementary regions A and A' is linked to a stretch of single-stranded nucleic acid C', wherein C' is complementary of C.

The inventors have surprisingly found that when said HP1 nucleic acid is denatured, in presence of the HP2 molecule containing the nucleic acid of interest, an entirely new nucleic acid is formed, wherein C and C' hybridize, as well as A of HP1 with A' of HP2, and A' of HP1 with A of HP2. The new nucleic acid molecule thus formed is a hairpin which is bound by its extremities to two different surfaces. One of said extremities comprises A of HP1 hybridised with A' of HP2, whereas the other extremity comprises the contiguous regions A' and C of HP1 respectively hybridised to the contiguous regions A and C' of HP2. The stem of the hairpin resulting from the process comprises the nucleic acid of interest. The hairpin thus formed behaves exactly like the hairpins constructed by the methods of the prior art. In particular, the hairpin of the invention is amenable to the same kind of single-molecule analysis as the hairpins of the prior art and under the same conditions (see e.g., WO 2011/147931; WO 2011/147929; WO 2013/093005; WO 2014/114687).

In a first aspect, the invention thus relates to a method for preparing a hairpin, said method comprising the steps of:
a) providing a nucleic acid HP1, said nucleic acid comprising:
 a first end bound to a first surface;
 a single-stranded region of sequence A linked to said first end;
 a single-stranded region of sequence A' hybridised to said single-stranded region A, wherein said single-stranded regions A and A' are not covalently linked;
 at least one single-stranded region of sequence C linked to said single-stranded region of sequence A';
 A second end linked to said single-stranded region of sequence C, wherein said second end is bound to a second surface;
b) providing at least one nucleic acid HP2, said nucleic acid comprising:
 a double-stranded region comprising the sequence of interest,
 a loop linked to a first end of said double-stranded region,
 a single-stranded region having the sequence A linked to a first strand of the second end of said double-stranded region, said region of sequence A being linked to a single-stranded region of sequence C', C' being complementary of C;
 a single-stranded polynucleotide having the sequence A' linked to a second strand of the second end of said double-stranded polynucleotide molecule, wherein the single-stranded polynucleotides of sequences A and A' are hybridised;
c) denaturing said nucleic acid HP1 of step c) in the presence of said nucleic acid HP2 of step b); and
d) obtaining a hairpin.

As used herein, 'hairpin' means a nucleic acid molecule comprising a region of intra-strand pairing linked to a loop. A 'loop', as used herein, refers to a succession of nucleotides of a strand of said nucleic acid that are not paired through hydrogen bonds with nucleotides of the same or another strand of said nucleic acid. The region of intra-strand pairing is usually referred to as a 'stem' and may comprise at least 1, preferably 2, more preferably 5, even more preferably 10, still more preferably 20 pairs of bases.

Preferably, obtaining a hairpin involves applying a physical force, such as e.g., a tension, to HP1. More preferably, said tension is obtained by pulling away the ends of HP1.

In a preferred embodiment, the single-stranded region of sequence A of said structure HP1 is linked to a single-stranded region of sequence D, said single-stranded region of sequence D being bound to said first surface. According to this embodiment, the single-stranded region of sequence A' of structure HP2 is linked to a single-stranded region having the sequence D', wherein D' is complementary to D.

According to this embodiment, the hairpin formed comprises a first extremity comprising the contiguous regions A and D hybridised to the contiguous regions A' and D' of HP2, and a second extremity comprising the contiguous regions A' and C of HP1 respectively hybridised to the contiguous regions A and C' of HP2.

Without being bound by theory, it can be hypothesized that the new hairpin structure is obtained by the formation of a Holliday junction between HP1 and HP2, followed by the resolution of said junction. A "Holliday junction", as used herein, refers to a four-way DNA junction, which is formed as a result of a reciprocal exchange of DNA strands between two nearly identical DNA molecules. Holliday junctions are generally accepted to be the central intermediate in homologous recombination. The resolution of these intermediates usually requires various enzymes (see e.g., Matos & West, *DNA Repair* (Amst). 19: 176-181, 2014). Importantly, no enzymatic activity is required for either forming or resolving the present Holliday junction. This is particularly advantageous, since it makes the process of forming the hairpin from the HP1 and HP2 nucleic acids irreversible as long as the tension is higher than 1 pN. Furthermore, even in the absence of a tension exerted on the bead, it is possible to ensure that the strand invasion is irreversible by creating a HP1 molecule comprising e.g. one or more mismatches and/or modified bases in the sequences of A and A'. Such a mismatch or modified bases, though insufficient to significantly destabilize the binding of the two components of HP1, will yet create an energetic barrier that will prevent the strand invasion processes of proceeding in the reverse direction once it has moved past this region.

The first step in the formation of a Holliday junction is the invasion of a double-stranded nucleic acid molecule by a single strand. The inventors have found that strand invasion of HP1 by HP2 is induced by a partial denaturation of HP1. By 'denaturation', it is herein meant the process of strands separation of a double-stranded nucleic acid molecule occurring when most of the hydrogen bonds between the said strands are broken. The denaturation process yields a denatured nucleic acid molecule, by which it is herein meant the two separated complementary strands resulting from the denaturation of a double-stranded nucleic acid molecule. The denaturation may be partial, i.e., some of the hydrogen bonds between the two strands remain intact, or total, wherein all of said hydrogen bonds are broken. By 'renaturation', it is herein referred to the process by which two separated complementary strands reform through hybridization into a double helix. As used herein, 'hybridization' is the process of establishing a non-covalent, sequence-specific interaction between two or more complementary strands of nucleic acids into a single hybrid.

There are several possibilities known to the skilled person to denature a nucleic acid. In a most preferred manner, the two strands are separated by submitting them to a physical force such as e.g., a tension. For example, the free ends of the said double-stranded nucleic acid may be pulled apart, thus rupturing all the bonds between the paired bases, and opening the double-stranded nucleic acid. This embodiment is particularly advantageous, as the inventors have found that exercising a small tension on the HP1 structure leads to a partial denaturation thereof, thus inducing strand invasion by HP2.

A "nucleic acid" as used herein refers to a single- or double-stranded linear polynucleotide containing either deoxyribonucleotides or ribonucleotides that are linked by 3'-5'-phosphodiester bonds. The nucleic acid of the invention can be in particular a DNA or an RNA molecule, either natural or modified. The terms "deoxyribonucleic acid" and "DNA" as used herein mean a polymer composed of deoxyribonucleotides. The terms "ribonucleic acid" and "RNA" as used herein mean a polymer composed of ribonucleotides. The said single-stranded nucleic acid may also be made of modified nucleotides, such as 2,6-Diaminopurine (2-AminodA), 5-Methyl dC, locked nucleic acid (LNA), which are nucleotides in which the ribose moiety is modified with an extra bridge connecting the 2' oxygen and 4' carbon, or Unlocked Nucleic Acids (UNAs) are acyclic RNA analogues without a C2'-C3' bond in the ribose ring. Said single-stranded nucleic acid can also comprise peptide nucleic acid (PNA), wherein the backbone is composed of repeating N-(2-aminoethyl)-glycine units linked by peptide bonds.

A nucleic acid according to the invention may be double-stranded and/or single-stranded. A double-stranded nucleic acid comprises two strands paired in anti-parallel orientation through hydrogen bonds, wherein the base sequence on one strand is complementary of the base sequence on the other strand. Most often, the double-stranded nucleic acid will be DNA, but it is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired. Furthermore, the duplex may consist of the at least partial re-pairing of two single strands obtained from samples of different origins. Finally, the invention also applies to the secondary structures of a sole single-stranded DNA or of a sole single-stranded RNA. The single-stranded nucleic acid of the invention can be in particular a DNA or an RNA molecule, either natural or modified.

In a preferred embodiment, the nucleic acid of the invention contains both regions which are double-stranded and regions which are single-stranded. In other words, in this embodiment, some regions of the nucleic acid are specifically paired to their complementary sequence in a duplex, while other regions are not hybridised. Such single-strand regions are thus free to hybridize with polynucleotides possessing complementary regions. In particular, the single-stranded region(s) of the nucleic acid HP2 is (are) free to hybridize with the complementary region(s) present in HP1, provided HP1 is partially denatured.

In a typical configuration, the nucleic acid HP1 is specifically anchored on two solid surfaces (e.g. microscope slide, micropipette, microparticle), one of which can be moved. In other words, one of the ends is attached directly or indirectly to a surface, while the other end is attached directly or indirectly to a movable surface. In this embodiment, a tension is applied on both ends of the HP1 molecule when the surfaces are moved away. When the tension is higher than a threshold value, the two strands of the double-stranded regions of HP1 are separated and the nucleic acid molecule is at least partially denatured, thus enabling strand invasion by the single-stranded regions of HP2. The tension applied is preferentially above or equal to 3 pN; it is more preferentially above or equal to 4 pN; it is even more preferentially above or equal to 5 pN; in a very much preferred aspect, it is above or equal to 6 pN. In a preferred embodiment, the tension applied is not sufficient for fully denaturing HP1. According to this embodiment, the tension applied is preferentially below or equal to 11 pN; it is more preferentially below or equal to 10 pN; it is even more preferentially below or equal to 9 pN; in a very much preferred aspect, it is below or equal to 8 pN. This force may vary with temperature, nucleotide type and buffer, but the skilled person will easily adapt the said force with regard to these parameters in order to obtain the partial separation of the two strands.

In a preferred embodiment, HP1 nucleic acid molecules are anchored at multiple points at one end to a motionless element, e.g. a surface, and at the other end to a movable surface, in this case a magnetic bead. Magnets are provided for acting on the bead. In particular, the magnets may be used for pulling the bead away from the surface. However, the implementation of the method of the invention is not restricted to the above apparatus. Any device which allows one to fully extend and then refold a molecule of double stranded nucleic acid, whilst monitoring at the same time the extension of the said molecule can be used to implement the method of the invention. For example, acoustic or optical tweezers may be used; they require however prior force calibration and are not easily parallelized for high throughput measurements. Further drawbacks of the optical tweezers are the lack of total torsional control of the nucleic acid and the possible local heating of the solution by the focussed laser which may alter the hybridization conditions.

It will be immediately apparent to the skilled person that the molecules of HP1 can be prepared in advance. For example, in a first step, a first nucleic acid molecule comprising a single-stranded region of sequence A and a second nucleic acid molecule comprising a single-stranded region of sequence A' and at least one single-stranded region of sequence C linked to said single-stranded region of sequence A', wherein A, A' and C are as defined above, can be prepared by conventional molecular biology techniques. The complementary regions A and A' are then allowed to hybridize. In another step, the two ends of HP1 are bound to two surfaces, on which can be moved (e.g., with acoustic, optical, or magnetic tweezers). This binding step and the hybridization step can be performed in any order, although it is preferred that the sequences A and A' have been allowed to form a duplex before the ends of the nucleic acid molecule are bound to the surfaces. The sequences A and A' can be of any length, provided they are long enough to maintain the two polynucleotides of HP1 together, without requiring the formation of a covalent bond. Preferably, each of said sequences comprises at least 30, more preferably 35, even more preferably 40, still more preferably 45 nucleotides. The combined regions A' and C and/or the combined regions A and D should be long enough for resisting the maximum shearing force produced by pulling on the ends of the hairpin. In particular, each of the sequences C and C' comprises at least 10, more preferably 12, even more preferably 13, still more preferably 14, most preferably 15 nucleotides. Likewise, the sequence D and the sequence D' each comprises at least 8, more preferably 10, even more preferably 11, still more preferably 12, most preferably 13 nucleotides.

The nucleic acid HP1 is incubated for a few minutes in a solution of adequate beads (for example streptavidin coated ones) to which it binds by one of its labelled (for example biotin) ends. The beads can be transparent if optical tweezers are later used for manipulation or magnetic if one uses magnetic traps or tweezers for manipulation. There is no restriction with regard to the nature of the beads for using acoustic beads.

The bead-nucleic acid assembly is injected in a fluidic chamber the surface of which has been treated such as to bind the other labelled end of the molecule (for example a surface coated with anti-Dig antibodies to bind the Dig-labelled end of the nucleic acid). The beads are thus anchored to the surface via the molecules of HP1. The distance of the bead to the surface is then monitored by various means known to the man of the art: for example the diffraction rings of their image on a camera can be used to deduce their distance, or the light intensity they scatter (or emit by fluorescence) when illuminated in an evanescent mode can be used to measure their distance. Alternatively, the magnetic field they generate can be measured (using a magnetic sensor such as GMR or Hall sensors) to deduce their distance to a sensor on the anchoring surface.

To pull on the nucleic acid molecule anchoring the beads to the surface various techniques have been described. One can use the light of a focused laser beam to trap a transparent bead near the focal point. By the relative translation of the beam with respect to the anchoring surface one can apply a force on the tethering molecule (a typical optical tweezers assay). The exerted force being proportional to the displacement of the bead from its equilibrium position, to exert a constant force on the tethering molecule requires a feedback loop on the trapping beam.

To exert a constant force on a bead, the use of the hydrodynamic drag generated by a flow around the bead has been described, but it usually yields a low spatial accuracy (>100 nm). The preferred embodiment uses a magnetic trap to pull on super-paramagnetic beads anchored to a surface by a nucleic acid hairpin as described above. In this configuration, small magnets placed above the sample are used to apply a constant force on the anchored bead, whose position can be determined with <1 nm accuracy (depending on the pulling force and the dissipation due to hydrodynamic drag)

In order to attach nucleic acids to surfaces or supports, use may be made of any one of the techniques known in the field. Essentially, the nucleic acid becomes anchored directly to the support, for example the micro-bead, which involves a functionalization of this surface, for example by coating it with streptavidin, a COOH group, and the like, capable of reacting with the functionalized end of the nucleic acid.

Such methods necessitate, in general, functionalizing the nucleic acid, especially the 3' and 5' ends, that is to say grafting appropriate chemical groups onto them. For this purpose, different procedures may be adopted. The simplest is to functionalize, using synthetic oligonucleotides, each of the ends of a HP1 with two different functions, which permit anchoring to two different pre-treated surfaces. This enables the two ends to be treated differently. For example, a first synthetic oligonucleotide containing a biotin at its 5' end may be used to obtain a first adapter, which is then linked to a first end of the HP1 molecule, thus enabling coupling to a streptavidin-coated surface. Likewise, a second synthetic oligonucleotide may be used to obtain a second adapter, said adapter containing Digoxigenin-labelled nucleotides. This second adapter may then be linked to a second end of the HP1 molecule, thus enabling coupling to an anti-Dig-antibody-coupled surface. Advantageously, said anti-Dig-antibody-coupled surface is different from the streptavidin-coated surface. Preferably, the bead has been coated with streptavidin, while said anti-Dig-antibody-coupled surface is the surface of the fluidic chamber into which the bead-nucleic acid complex is injected. The resulting HP1 molecules are thus anchored through a first end to the bead and through the other end to the flow cell. The advantage of this method lies in its capacity to separately functionalize a heterogeneous population of large nucleic acid fragments (as are obtained by fractionation of a gene or chromosome), during the production of a library of HP2 precursors. These can then be analysed simultaneously.

The drawback of this method lies in the steric interference between the two adjacent functional groups, which can make coupling to the surfaces difficult. To solve this problem, it can be advantageous to add at each free end of the hairpin molecule a "spacer" sequence of bases, to the end of which a functional group is then added; the two spacer sequences are non-complementary, affording each functional group enough space to bind to its dedicated surface. In addition, said spacers serve to keep the nucleic acid further away from the surface of the bead or flow cell, and thus minimize electrostatic repulsion. More advantageously, the sequence of each spacer sequence is designed in order to use single-stranded sequencing primers of known sequence in the sequencing method of the invention. These spacers can be single stranded or double stranded or a mixture of both. Double stranded spacers are preferred since they are more rigid, which helps to keeps the hairpin away from the surfaces. Moreover, if a nick (i.e., a break in the phosphodiester backbone) appears in a long double-stranded nucleic acid, the functionality of the hairpin may be preserved, i.e., such a nicked hairpin may still be used for analytic purposes in the methods previously developed by the inventors (see e.g., WO 2011/147931; WO 2011/147929; WO 2013/093005; WO 2014/114687).

Methods for preparing such spacers and adding them to HP1 are well known to the person skilled in the art and need thus not be detailed here.

As regards the actual anchoring techniques, there are many of these and they derive from the techniques for anchoring macromolecules (proteins, DNA, and the like) to commercially available pretreated surfaces. Most of these techniques have been developed for immunology tests, and link proteins (immunoglobulins) to surfaces carrying groups (—COOH, —NH$_2$, —OH, and the like) capable of reacting with the carboxyl (—COOH) or amine (—NH$_2$) ends of proteins.

The covalent anchoring of nucleic acid may be accomplished directly, via the free phosphate of the 5' end of the molecule, which reacts with a secondary amine (Covalink —NH surface marketed by Polylabo at Strasbourg) to form a covalent bond. It is also possible to functionalize DNA with an amine group and then to proceed as with a protein.

There are also surfaces coated with streptavidin (Dynal beads, and the like), which permit quasi-covalent anchoring between the streptavidin and a biotinylated DNA molecule. Lastly, by grafting an antibody directed against digoxigenin onto a surface (by the methods mentioned above), a nucleic acid functionalized with digoxigenin may be anchored thereto. This represents merely a sample of the many possible anchoring techniques (see e.g., Janissen et al., *Nucleic Acids Res.* 42(18):e13, 2014).

Among the attachment and anchoring techniques, there should also be mentioned, for example, the techniques described in Patent EP 152 886 using an enzymatic coupling for the attachment of DNA to a solid support such as cellulose.

Patent EP 146 815 also describes various methods of attachment of DNA to a support.

Similarly, patent application WO 92/16659 proposes a method using a polymer to attach DNA.

Naturally, the nucleic acid may be attached directly to the support but, where necessary, especially with a view to limiting the influence of the surfaces, the nucleic acid may be attached at the end of an inert arm of peptide or other nature, as is, for example, described in Patent EP 329 198.

Substrates or supports for use in the invention include, but are not limited to, latex beads, dextran beads, polystyrene surfaces, polypropylene surfaces, polyacrylamide gel, gold surfaces, glass surfaces and silicon wafers. In certain embodiments, the solid support may include an inert substrate or matrix that has been functionalized, for example by the application of a layer or coating of an intermediate material including reactive groups that permit covalent attachment to molecules such as polynucleotides.

In a preferred embodiment, the substrate for use in the invention enables the attachment of several independent HP1 molecules at discrete locations, so as to allow the simultaneous construction of a great number of hairpins by the method of the invention, thus enabling the simultaneous analysis of a great number of nucleic acid molecules. Thus, according to this embodiment, more than one HP1 molecules, for example, at least two or three or four or more, HP1 molecules may be grafted to the solid support. For example, the HP1 molecule is advantageously bound to the surface of each of the wells of a microarray. In this manner, a library of nucleic acid sequences of interest can be utilized in the method of the invention with the HP1 molecules bound to the surface to prepare a library of hairpins. This library of hairpins, wherein each hairpin contains a specific nucleic acid sequence, is suitable for use in applications usually carried out on ordered arrays such as micro-arrays. Such applications by way of non-limiting example include hybridization analysis, gene expression analysis, protein binding analysis, sequencing, genotyping, nucleic acid methylation analysis and the like (WO 2011/147931; WO 2011/147929; WO 2013/093005; WO 2014/114687). The clustered array may be sequenced before being used for downstream applications such as, for example, hybridization with RNA or binding studies using proteins.

Common molecular biology techniques can be used to prepare the molecules of HP2 by ligating a loop to the nucleic acid of interest. Likewise, the other extremity of the nucleic acid of interest may be ligated to the regions A and A' using only usual methods of molecular biology. For example, an oligonucleotide comprising the regions A and C' may be synthesized and hybridised to another oligonucleotide, said other oligonucleotide having the sequence A'. This results in a double-stranded polynucleotide with a single-stranded overhang. Said polynucleotide can then be ligated to the nucleic acid of interest.

The nucleic acid of interest according to the invention may be any type of nucleic acid. The nucleic acid of interest can be synthetic or derived from naturally occurring sources, or may include both synthetic and natural sequence; and may include PCR products. In this particular embodiment, said nucleic acid of interest is a single species of nucleic acid, i.e., all the molecules of said nucleic acid are identical. In this case, all the molecules of HP2 will be identical and therefore all the hairpins prepared by the method of the invention will likewise be identical.

In another embodiment, the nucleic acid of interest represents a population of double-stranded nucleic acid molecules. This is the case, for example, when a library of nucleic acid sequences, such as e.g., a genomic library or an expression library is used to prepare the HP2 molecules. This results in a population of HP2 molecules wherein each molecule is distinct from the other, thus generating with the method of the invention a population of unique hairpins which can be directly analysed or sequenced by the methods devised by the inventors (WO 2011/147931; WO 2011/147929; WO 2013/093005; WO 2014/114687). According to this embodiment, the molecules of the nucleic acid of interest are for example isolated from a biological sample containing a variety of other components, such as proteins, lipids and non-template nucleic acids. A "biological sample" may be any sample which may contain a biological organism, such as, for example, bacteria, viruses, plants, yeasts etc. A "biological sample" according to the invention also refers to a sample which may be obtained from a biological organism, such as a cellular extract obtained from bacteria, viruses, plants, yeasts etc. Molecules of the nucleic acid of interest can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Molecules of the nucleic acid of interest can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. Nucleic acid obtained from biological samples typically is fragmented to produce suitable fragments for analysis. In one embodiment, nucleic acid from a biological sample is fragmented by sonication. Molecules of the nucleic acid of interest can be obtained as described in US 2002/0190663. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, individual nucleic acid template molecules can be from about 1 base to about 20 kb. These individual molecules are then used to prepare the HP2 molecules as described above. Thus in this embodiment, the method of the invention comprises using a plurality of distinct HP2.

In another aspect, the present invention provides a HP1 and a HP2 molecule for use in the method described above.

The present invention also provides a hairpin obtained by the method of the invention. Said hairpin comprises:

A first end bound to a first surface,

A first double-stranded region linked to said first end, wherein said first double-stranded region comprises a first strand comprising a region A and a second strand comprising a region A', wherein A and A' are hybridised;

A stem-and-loop region linked to said first double-stranded region, wherein said stem comprises the nucleic acid of interest;

A second double-stranded region linked to said stem-and-loop region, wherein said second double-stranded region comprises a first strand comprising a region A and a region C' and a second strand comprising a region A' and a region C, wherein the regions A and C' are hybridized with the regions A' and C, respectively;

A second end linked to said second double-stranded region, wherein said second end is bound to a second surface.

In a preferred embodiment, said first double-stranded region comprises a first strand comprising a region A and a region D and a second strand comprising a region A' and a region D', wherein the regions A and D are hybridised with the regions A' and D', respectively In another preferred embodiment, one of the surfaces is a movable surface, as described above.

The hairpin of the invention comprises a double-stranded stem and an unpaired single-stranded loop. In a hairpin, the ends of the two strands which are not engaged in the loop are free and can thus be pulled apart. This results in the unpairing of the double stranded nucleic acid stem, thus yielding a denatured double stranded nucleic acid molecule. It is possible to open completely a hairpin double-stranded nucleic acid molecule by pulling on each end of the said nucleic acid molecule with a force higher than a threshold value. When the tension applied to the molecule is decreased to an intermediate value, the nucleic acid molecule self-rehybridises to reform a hairpin.

It is advantageous in this respect to design the loop sequence and length so that the hairpin refolds after a short transient, e.g. 1 s. Methods to this effect have been described in the prior art, e.g. in Woodside et al., *Proc. Natl. Acad. Sci. U.S.A.*, 103 (16): 6190-6195, 2006). When the force is decreased from the opening to the test value, the extension of the open hairpin varies because of the elasticity of single stranded DNA. The small delay before the hairpin refolds allows the user to determine the hairpin extension at the same force as the one used to detect the blocking state.

The hairpin formed by the method of the invention can be denatured and renatured, as usual for hairpin structures, and is suitable for all mapping and sequencing experiments. For example, if one of the two surfaces is a movable surface, pulling said movable surface away from the other generates a tension which results in a hairpin molecule which is denatured at least partially. In fact, the inventors have surprisingly found that the length of the complementary sequence (AC/A'C', and A'/A; or A'C/AC' and A/A') is long enough to resist the shearing force of the movement of the surface, as opposed to the smaller length of complementary sequence found in the Holliday junction.

Therefore, in yet another aspect, the invention relates to a method of analysis of the nucleic acid of interest comprised in the hairpin obtained by any of the method described above.

For example, the hairpin can be used for detecting the nucleic acid of interest. According to this embodiment, when a single-stranded nucleic acid molecule is added to a denatured double-stranded nucleic acid prior to renaturation, a blockage of rehybridization indicates that the sequence of the single-stranded nucleic acid molecule is complementary to at least part of the sequence of the double-stranded nucleic acid molecule.

This single-stranded nucleic acid can be of any length, provided that it is long enough to block the renaturation process. Preferentially, the length of the single stranded nucleic acid will be comprised between 3 and 50 nucleotides; more preferentially, between 3 and 45 nucleotides, between 3 and 40 nucleotides, between 3 and 35 nucleotides, between 3 and 30 nucleotides, between 3 and 25 nucleotides, between 3 and 20 nucleotides, between 3 and 15 and even more preferentially between 3 and 12. The single-stranded nucleic acid of the invention can be in particular a DNA or an RNA molecule, either natural or modified. Said single-stranded nucleic acid may also be made of modified nucleotides, such as 2,6-Diaminopurine (2-Amino-dA), 5-Methyl dC, locked nucleic acid (LNA), which are nucleotides in which the ribose moiety is modified with an extra bridge connecting the 2' oxygen and 4' carbon, or Unlocked Nucleic Acids (UNAs) are acyclic RNA analogues without a C2'-C3' bond in the ribose ring. Said single-stranded nucleic acid can also comprise peptide nucleic acid (PNA), wherein the backbone is composed of repeating N-(2-aminoethyl)-glycine units linked by peptide bonds. In another embodiment, the said single-stranded nucleic acid may also contain a modification at the end of the oligo (5' or 3') that improves binding. Well known examples of such modifications include the MGB (Minor Groove Binder), acridine (an intercalator) and ZNA (i.e., zip DNA, a spermine derivative).

Thus, the method of the invention also relates to a method for detecting said nucleic acid sequence, said method comprising the steps of:
a) denaturing a hairpin molecule as described above, said hairpin potentially comprising said nucleic acid sequence, by applying a physical force to said hairpin molecule;
b) providing a single-stranded nucleic acid molecule;
c) renaturing the said hairpin molecule in the presence of the said single-stranded nucleic acid molecule
d) detecting a blockage of the renaturation of the hairpin.

Preferably, the physical force of step a) is a tension, which is applied by moving away the supports. When the tension is higher than a threshold value, the two strands are separated and the nucleic acid molecule is denatured. The tension applied is preferentially above or equal to 15 pN; it is more preferentially above or equal to 16 pN; it is even more preferentially above or equal to 17 pN; in a very much preferred aspect, it is above or equal to 18 pN. This force may vary with temperature, nucleotide type and buffer, but the skilled person will easily adapt the said force with regard to these parameters in order to obtain the separation of the two strands. On the other hand, when the tension is decreased under a minimal value, the two strands of the denatured double-stranded nucleic acid can rehybridise. To obtain rehybridization of the said two strands, a tension of less than or equal to 12 pN is preferentially applied; more preferentially, it is less than or equal to 11 pN; even more preferentially, it is less than or equal to 10 pN. Preferably, said tension is higher than 1 pN, to prevent reversibility of strand invasion. Alternatively, the tension may be as low as 0 pN when the HP1 molecule comprises one or more mismatches and/or modified bases can be introduced in the sequences of A and A', which is insufficient to significantly destabilize the binding of the two components of HP1, and yet will create an energetic barrier that will prevent the strand invasion processes of proceeding in the reversible direction once it has moved past this region.

Using a hairpin makes it possible, in particular, to perform cycles of pairing and unpairing and thus to improve the signal/noise ratio.

By determination of the blockage, it is herein meant the determination of the physical parameters associated with the blockage. The most useful of these parameters is the position of the blockage on the double-stranded nucleic acid molecule, said position corresponding to the position of hybridization of the single-stranded nucleic acid molecule on the double-stranded nucleic acid molecule. Indeed, the inventors have found that the position on the double-stranded nucleic acid at which the pause in renaturation occurs can be precisely determined: the use of a hairpin affords the skilled person a means to determine the physical distance between the two free ends of the hairpin at any time during the denaturation/renaturation process.

By 'free end' it is herein meant the end of one strand which is not covalently linked to an extremity of the other strand; as explained above, these free ends are each bound to a different surface. In particular, one of these surfaces is movable, whilst the other may be motionless. The skilled person will thus easily realize that, in order to measure the distance between the free ends of the hairpin, it is possible to simply measure the distance between the two surfaces.

This distance is maximal ($z_{high}$ ($F_{open}$)) when the hairpin molecule is completely denatured, since the hairpin nucleic acid is then completely extended; it is minimal ($z_{low}$ ($F_{test}$)) when the said hairpin molecule is completely renatured. It is advantageous to perform all length comparisons at the same force $F_{test}$, so that the single stranded nucleic acid has the same elastic properties. Using the delay in loop closing the skilled user can measure $z_{high}$ ($F_{test}$). Likewise, the distance between the two free ends when the renaturation process is temporarily paused can be measured: as expected, this distance z is comprised between $t_{high}$ and $z_{low}$ (all z being measured with $F=F_{test}$). It is immediately clear that the distance z varies with the localization in the hairpin molecule of the sequence to which the sequence of the single-stranded nucleic acid is complementary. If the said single-stranded nucleic acid hybridises with a sequence which is located close to the free ends of the hairpin, the self-rehybridization process is blocked just before the complete hairpin is reformed; in this case, $z_{pause}$ is minimal. On the other hand, if the said single-stranded nucleic acid hybridises with a part of the hairpin which is close to the unpaired loop, the renaturation process will be arrested in a situation where the hairpin is completely, or almost completely denatured; in this case, $z_{pause}$ is maximal.

It is possible to correlate precisely a physical distance in a double-stranded nucleic acid molecule with a number of bases. For example, a distance of 1 nm corresponds to the distance spanned by two nucleotides (1 bp) in a nucleic acid under a 10 pN force. The exact calibration versus force is given by the elasticity of single stranded nucleic acid. Therefore, by simply measuring the distance between the two free ends of the hairpin molecule, it is possible to determine precisely where the renaturation is blocked.

In a preferred embodiment, the detection of the blockage of the renaturation of the said hairpin involves determining the position of the blockage on the hairpin, as described above.

Thus, in one embodiment, the invention consists of a method for determining the sequence of a nucleic acid, wherein the hairpin molecule comprising the sequence to be determined is first denatured by application of a physical force, then rehybridised in a presence of a single-stranded nucleic acid, and the presence of a blockage in the rehybridization detected. In one aspect, the distance between the two ends of the hairpin is determined when the renaturation process is blocked. Preferentially, the distance between the two ends of said hairpin is determined when the molecule is completely denatured. Even more preferentially, the two distances are compared and the position of the blockage is determined.

According to this particular embodiment, the method for determining the sequence of a nucleic acid comprises the steps of:
a) denaturing a hairpin obtained by the method described above, said hairpin comprising said nucleic acid sequence, by moving away the surfaces;
b) measuring the distance $Z_{high}$ between the two ends of the denatured hairpin molecule obtained in step a);
c) hybridizing a single-stranded nucleic acid molecule, the primer, with said denatured hairpin molecule obtained in step a);
d) renaturing said hybridised single-stranded nucleic acid molecule/hairpin molecule of step c); and
e) detecting a blockage of the renaturation of the hybridised single-stranded nucleic acid molecule/hairpin molecule; and
f) determining the position of said blockage with respect to one end of the hairpin, said determination comprising the steps of:
   measuring distance (z) between the two ends of the hairpin molecule which are attached to a support, comparing z and $Z_{high}$, and
   determining the position of the blockage;
wherein said nucleic acid sequence is derived from the position of said blockage.

In a particular embodiment, the sequencing of the nucleic acid of interest contained in the hairpin molecule of the invention involves the replication of said nucleic acid with a polymerase. For example, the polymerase reaction may be performed in presence of a pool of deoxy-nucleotides (dNTP) where one of the bases is present at a very low concentration. In that case, each time the polymerase encounters the complement of the said nucleotide, it pauses until the low concentration nucleotide diffuses into position (Greenleaf and Block, Science, 313: 801, 2006; U.S. Pat. No. 7,556,922). Alternatively, it is possible to use dideoxy-nucleotides (ddNTPs) in addition to the normal deoxynucleotides (dNTPs) found in DNA. Incorporation of one ddNTP causes the polymerase reaction to stop, since no nucleotide can be added after the said ddNTP. The position of each pause or blockage can then be determined by the method of the invention, i.e. by measuring the physical distance between the two free ends of the molecule, thus leading to the identification of the sequence of the nucleic acid contained in the hairpin of the invention. Further embodiments of this method can be found in WO 2011/147929.

Another useful parameter associated with the blockage in renaturation is the period of time during which the renaturation is blocked (referred herein as the duration of the pause in renaturation). Indeed, it is possible to measure the period of time during which the rehybridization is blocked. For example, the skilled person can determine the period of time during which the distance between the two ends of the hairpin is z as defined above, i.e. an intermediate value comprised between $Z_{high}$ and $Z_{low}$.

Thus, in one particular embodiment, the method for determining the sequence of a nucleic acid comprises the steps of:
denaturing the said hairpin molecule comprising said nucleic acid sequence by applying a physical force to said hairpin;
providing a single-stranded nucleic acid molecule,
renaturing the hairpin molecule in the presence of the said single-stranded nucleic acid molecule; and
detecting a blockage of the renaturation of said hairpin, and
determining the duration of said blockage.

The duration of the blockage is dependent upon the degree of complementarity between the two sequences. The higher the complementarity, the greater the number of bonds established between the two molecules, and therefore the longer the duration.

In this particular embodiment, the method according to the present invention may thus be used for diagnostic purposes. In particular, it is possible to provide for a simplified technique, based on the observation that a mismatch between the single-stranded nucleic acid and the sequence of interest results in a much shorter lived hybridization. In a first aspect, the renaturation of a hairpin is blocked by a single-stranded nucleic acid, by any of the methods described above, and the duration of the blockage is determined. In a preferred aspect, this value is compared to a reference value. In a further preferred aspect, the reference value corresponds to the length of the pause observed with a reference single-stranded nucleic acid, as determined by any of the above methods.

In this embodiment, the invention relates to a method for detecting the presence of a specific nucleic acid sequence, said method comprising the steps of:
- a) denaturing a hairpin obtained by the method described above, said hairpin potentially comprising said sequence, by moving away the surfaces;
- b) measuring the distance $Z_{high}$ between the two ends of the denatured hairpin molecule obtained in step a);
- c) hybridizing a single-stranded nucleic acid molecule, the primer, with said denatured hairpin molecule obtained in step a);
- d) renaturing said hybridised single-stranded nucleic acid molecule/hairpin molecule of step c); and
- e) detecting a blockage of the renaturation of the hybridised single-stranded nucleic acid molecule/hairpin molecule; and
- f) determining the position of said blockage with respect to one end of the hairpin, said determination comprising the steps of:
  measuring distance (z) between the two ends of the hairpin molecule which are attached to a support,
  comparing z and $Z_{high}$, and
  determining the position of the blockage;
- g) determining the duration of said blockage, wherein the presence of said nucleic acid sequence is derived from the position of said blockage and the duration of said blockage.

This method is particularly useful since it enables the detection of one single molecule within a whole population of nucleic acid molecules. Because of the single-molecule resolution obtainable with the method of the invention, each molecule carrying a specific sequence can be detected. Thus the present invention affords the skilled person to numerate the number of nucleic acid molecules carrying the said sequence. The present method allows for the easy and accurate quantification of a specific nucleic acid sequence in a whole population of nucleic acid molecules.

The method of the invention is particularly suited for generating a library of hairpins, each hairpin comprising a specific nucleic acid molecule. This method is thus particularly convenient for detecting a sequence of interest, e.g. a particular allele, within a whole population of nucleic acid molecules, for example in a biological sample. In this embodiment, a library of hairpins is obtained by the method described above, wherein said hairpin library represent a whole population of nucleic acids. Each of the hairpins of said library is then denatured by applying a tension to the ends of said hairpins, e.g., by moving away the surfaces. A single-stranded nucleic molecule comprising the sequence of interest is provided and allowed to hybridise to the denatured hairpin molecules. The hairpins are then renatured in the presence of said single-stranded nucleic acid molecule by e.g., reducing the tension applied to the ends. A pause in the renaturation of the hairpin is detected, and the duration of said pause is determined. According to this embodiment, the longest pause will be observed for the hairpin(s) comprising a nucleic acid whose sequence is exactly complementary of the sequence of interest. Because of the single-molecule resolution obtainable with the method of the invention, each molecule carrying a specific sequence can thus be detected. Thus the present invention affords the skilled person to numerate the number of nucleic acid molecules carrying the said sequence. Further embodiments and applications of the present method for the easy and accurate quantification of a specific nucleic acid sequence in a whole population of nucleic acid molecules can be found in WO 2013/093005.

In another embodiment, the hairpins of the invention are used for detecting the binding of a protein to a specific sequence. According to this embodiment, the invention relates to a method for the determination of the binding of a protein to a sequence of interest, said sequence being contained within a hairpin obtained by the method described above, wherein said method comprises a step of blocking the renaturation of said hairpin. More specifically, the hairpin is first denatured by applying a physical force, such as e.g., a tension, to said molecule (e.g., by moving away the surfaces to which the ends of said hairpin are bound). The protein is then provided and, optionally, a single-stranded nucleic acid molecule corresponding to said sequence. Said protein is allowed to bind to the sequence of interest (either as a denatured single-stranded hairpin, or a as a duplex between said denatured hairpin and said single-stranded nucleic acid molecule), before the hairpin is renatured by reducing the tension. A pause in the renaturation of the hairpin is detected, and the localization of said pause is determined as indicated above. Optionally, the duration of the pause is also determined.

The terms 'protein', 'proteins', 'polypeptide', and 'polypeptides', as used herein, are synonyms and refer to polymers of amino acids covalently linked through peptide bonds into a chain. Proteins can have several functions. A 'binding protein' is a protein which is capable of binding non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form multimers) and/or it can bind to one or more molecules of a different protein or proteins. A binding protein can have more than one type of binding activity. For example, zinc finger proteins have DNA-binding, RNA-binding and protein-binding activity. A 'nucleic acid-binding protein' according to the invention is thus a protein which is capable of interacting with a nucleic acid. A 'single-stranded nucleic acid-binding protein' according to the invention is thus a protein which is capable of interacting with a single-stranded nucleic acid, while a 'double-stranded nucleic acid-binding protein' according to the invention is thus a protein which is capable of interacting with a double-stranded nucleic acid.

In a first embodiment of the method of the invention, the protein which is used to block the renaturation of the denatured hairpin is a protein which is capable of binding single-stranded nucleic acid. According to this embodiment, the method of the invention thus relates to a method for the determination of the binding of a protein to a nucleic acid sequence, said method comprising the steps of:
  denaturing a said hairpin molecule comprising the said sequence by applying a physical force to the said molecule;
  providing the said protein;
  renaturing said hairpin molecule in the presence of the said protein and
  detecting a blockage of the renaturation of the hairpin.

Advantageously, the said method comprises the further step of determining the position of the blockage.

In this embodiment, the invention relates to a method for the determination of the binding of single-stranded nucleic acid-binding protein to a nucleic acid sequence, said method comprising the steps of:
- a) denaturing a hairpin obtained by the method described above, said hairpin potentially comprising said sequence, by moving away the surfaces;

b) measuring the distance $Z_{high}$ between the two ends of the denatured hairpin molecule obtained in step a);
c) contacting said protein with said denatured hairpin molecule obtained in step a);
d) renaturing said hairpin molecule of step d) in the presence of said protein; and
e) detecting a blockage of the renaturation of the hairpin molecule; and
f) determining the position of said blockage with respect to one end of the hairpin, said determination comprising the steps of:
   measuring distance (z) between the two ends of the hairpin molecule which are attached to a support, comparing z and $Z_{high}$, and
   determining the position of the blockage;
g) determining the duration of said blockage,
wherein the binding of said single-stranded nucleic acid-binding protein to said nucleic acid sequence is derived from the position of said blockage and the duration of said blockage.

In another embodiment of the method of the invention, the protein binds double-stranded nucleic acid. The inventors have shown that when a double-stranded nucleic acid-binding protein is present, it is capable of binding the hybrid formed between a denatured hairpin and a single-stranded nucleic acid molecule. This interaction between the protein and the nucleic acid hybrid leads an alteration of the duration of the blockage. Most of the time, this interaction leads to an increased blockage of the renaturation. For example, a primase will stabilize DNA oligos that would not otherwise have been sufficiently stable to block a hairpin re-hybridization for a time long enough to be detected. Likewise, the binding of a DNA-polymerase to the 3' end of a small oligonucleotide used as a primer increases its stability. Alternatively, the duration of the blockage may also be reduced. Indeed, the present inventors have shown that the binding of some helicases trigger a destabilization of the said hybrid, which is translated in a shorter blockage time.

According to this preferred embodiment, the method of the invention thus comprises the steps of:
a) denaturing a hairpin molecule comprising a specific sequence by applying a physical force to the said molecule;
b) providing the said protein and a single-stranded nucleic acid molecule corresponding to the said nucleic acid sequence;
c) renaturing the said hairpin molecule in the presence of the said protein and the said single-stranded nucleic acid molecule; and
d) detecting a blockage of the renaturation of the hairpin.

Advantageously, the said method comprises the further step of determining the position of the blockage.

In this embodiment, the invention relates to a method for the determination of the binding of double-stranded nucleic acid-binding protein to a nucleic acid sequence, said method comprising the steps of:
a) denaturing a hairpin obtained by the method described above, said hairpin potentially comprising said sequence, by moving away the surfaces;
b) measuring the distance $Z_{high}$ between the two ends of the denatured hairpin molecule obtained in step a);
c) hybridizing a single-stranded nucleic acid molecule with said denatured hairpin molecule obtained in step a);
d) contacting said protein with said hybridised single-stranded nucleic acid molecule/hairpin molecule of step c);
e) renaturing said hybridised single-stranded nucleic acid molecule/hairpin molecule of step c) in the presence of said protein; and
f) detecting a blockage of the renaturation of the hairpin molecule; and
g) determining the position of said blockage with respect to one end of the hairpin, said determination comprising the steps of:
   measuring distance (z) between the two ends of the hairpin molecule which are attached to a support, comparing z and $Z_{high}$, and
   determining the position of the blockage;
h) determining the duration of said blockage,
wherein the binding of said double-stranded nucleic acid-binding protein to said nucleic acid sequence is derived from the position of said blockage and the duration of said blockage.

This embodiment is particularly advantageous because it allows for the determination of the binding of the said protein to the sequence comprised within the double-stranded nucleic acid. It is possible to sequence directly the molecule bound by the said protein, without altering the setup of the experiment, by just replacing the buffer containing the protein and optionally a complementary single-stranded nucleic acid, by a buffer suitable for sequencing according to the method described above. The present method for determining the binding of a protein to a sequence can thus be used to identify the binding site of said protein. This method can notably be used for performing a genome-wide mapping of the binding sites of a specific nucleic acid-binding protein, such as e.g., a transcription factor. In this context, it is particularly advantageous to use a library of hairpins, wherein said hairpin library represent a whole population of nucleic acids corresponding to the totality of the genome.

Another particular application of the method of the invention is in the detection of epigenetic modifications. The present invention provides an easy method for detecting epigenetic modifications of nucleic acids. By 'epigenetic modifications', it is herein referred to modifications of the bases constituting a nucleic acid molecule which take place after the synthesis of said nucleic acid molecule. Such epigenetic modifications include, inter alia, 4-methylcytosine (m4C), 5-methylcytosine (5mC), 5-hydroxymethylcytosine (5hmC), 5-formylcytosine (5fC) and 5-carboxylcytosine (5caC), as well as 6-methyladenosine (m6A) in DNA, and 5-hydroxymethyluracil (5hmU) and N6-methyladenosine (m6A) in RNA.

Likewise, the method of the invention allows the detection of modified bases resulting from nucleic acid damage, preferably DNA damage. DNA damage occurs constantly because of chemicals (i.e. intercalating agents), radiation and other mutagens. DNA base modifications resulting from these types of DNA damage are wide-spread and play important roles in affecting physiological states and disease phenotypes. Examples include 8-oxoguanine, 8-oxoadenine (oxidative damage; aging, Alzheimer's, Parkinson's), 1-methyladenine, 6-O-methylguanine (alkylation; gliomas and colorectal carcinomas), benzo[a]pyrene diol epoxide (BPDE), pyrimidine dimers (adduct formation; smoking, industrial chemical exposure, UV light exposure; lung and skin cancer), and 5-hydroxycytosine, 5-hydroxyuracil, 5-hydroxymethyluracil, and thymine glycol (ionizing radiation damage; chronic inflammatory diseases, prostate, breast and colorectal cancer).

According to these embodiments, the presence of at least one modified base in the sequence of interest contained in the hairpin of the invention is identified by the detection of the binding of protein recognizing specifically said modified base (e.g., an antibody directed against said base) to said hairpin by the method described above.

These embodiments are particularly advantageous since all the occurrences of a specific modification in a genome can thus be identified and mapped accurately. In this context, it is particularly advantageous to use a library of hairpins, wherein said hairpin library represent a whole population of nucleic acids corresponding to the totality of the genome.

Further embodiments and applications of the present method for the detection of the binding of a protein to a specific nucleic acid sequence can be found in WO 2014/114687.

The practice of the invention employs, unless other otherwise indicated, conventional techniques or protein chemistry, molecular virology, microbiology, recombinant DNA technology, and pharmacology, which are within the skill of the art. Such techniques are explained fully in the literature. (See Ausubel et al., Current Protocols in Molecular Biology, Eds., John Wiley & Sons, Inc. New York, 1995; Remington's Pharmaceutical Sciences, 17th ed., Mack Publishing Co., Easton, Pa., 1985; and Sambrook et al., Molecular cloning: A laboratory manual 2nd edition, Cold Spring Harbor Laboratory Press—Cold Spring Harbor, N.Y., USA, 1989).

The examples below will enable other features and advantages of the present invention to be brought out.

LEGENDS OF THE FIGURES

FIG. 1: Structure of DNA hairpins used in magnetic tweezer analysis. A typical DNA hairpin structure is shown. The bold sequence represents the double stranded DNA region of interest, and the various DNA linkers required for functionality are described. Linker 1 is a small DNA loop that permanently attaches the 5'end of one strand of the ROI to the 3' end of the other strand. The structure will readily bind to a streptavidin-coated bead, by virtue of the Biotin moiety (shown as a red dot) synthesised on the end of linker 2. Finally, linker 3 allows binding to the flow cell surface coated in anti-digoxigenin antibodies, through the interaction with the digoxigenin located at its end (green dot).

Figure 2:
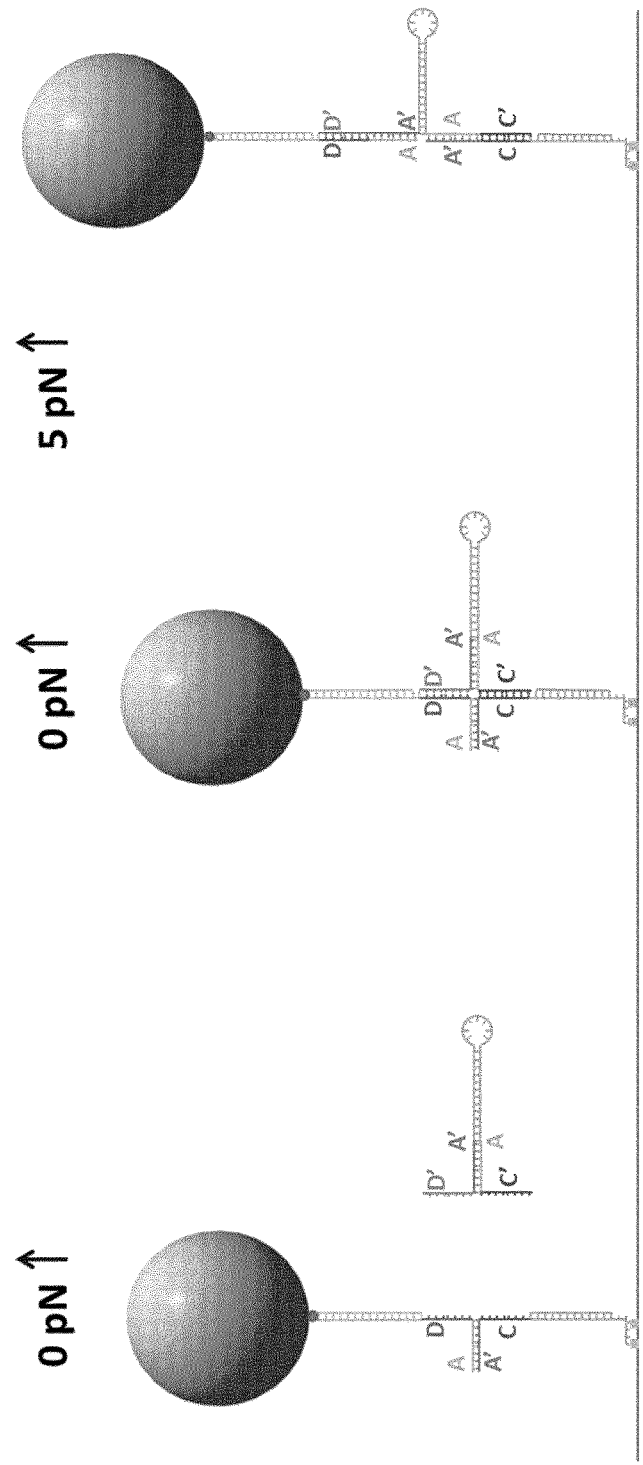

FIG. 2: Principle of the stand invasion process. On the far left a universal precursor hairpin-bead construct (HP1) is shown, which can be prepared in bulk and attached to the surface of the flow cell. It has a dsDNA linker attached to the bead, ending with a ssDNA overhang of sequence D-A. A second molecule consists of a dsDNA region with a digoxigenin-labelled tail allowing it to bind to the glass surface of the flow cell (dig represented by orange squares). The other end has a ssDNA region with a sequence C (of 12 nts) plus the 40 nt complementary sequence to A (A'). These two molecules (bead+linker and dig labelled linker) can be pre-incubated so that they hybridise together via the A and A' sequences, forming pre-hairpin structure HP1. This construct will be stable under normal conditions, but pulling on the magnetic bead with a force greater than a few pN will unzip the hybridised region and dissemble the structure. Next to this construct is displayed the structure called hairpin precursor HP2. It consists of the (double stranded) DNA to be studied (in grey) ligated to a loop at one end (shown on the right) and an adaptor at the other. The adaptor consists of 2 oligos hybridised together via A and A' sequences (identical to those on the hairpin shown in the left panel). The adaptor also has overhanging single stranded regions of sequences D' and C' that are complementary to sequences C and D of HP1, respectively. When a library of these hairpins (HP2) is introduced to a flowcell containing a plurality of the structures shown in the left panel, they will hybridise through their flaps (C' and D') each forming a Holiday junction with 2 nicks, called here HP3 (as shown in the middle right panel). When a small force (~5 pN) is applied to the bead, the Holiday junction rapidly migrates, lengthening the molecule and leading to a stable hairpin construction (shown in the far right panel). The molecule shown in the right panel is essentially identical to that shown in FIG. 1; it can be zipped and unzipped as usual for such hairpin structures, and is suitable for all mapping and sequencing experiments. Note that although there are 3 single stranded nicks in this molecule, the length of complementary sequence (AD-A'D' and CA'-C'A) is long enough to resist the shearing force of the magnet (as opposed to the smaller length of complementary sequence found on the uninvaded Halliday structure (held together only by 12 bp D-D' and C-C').

Figure 3:
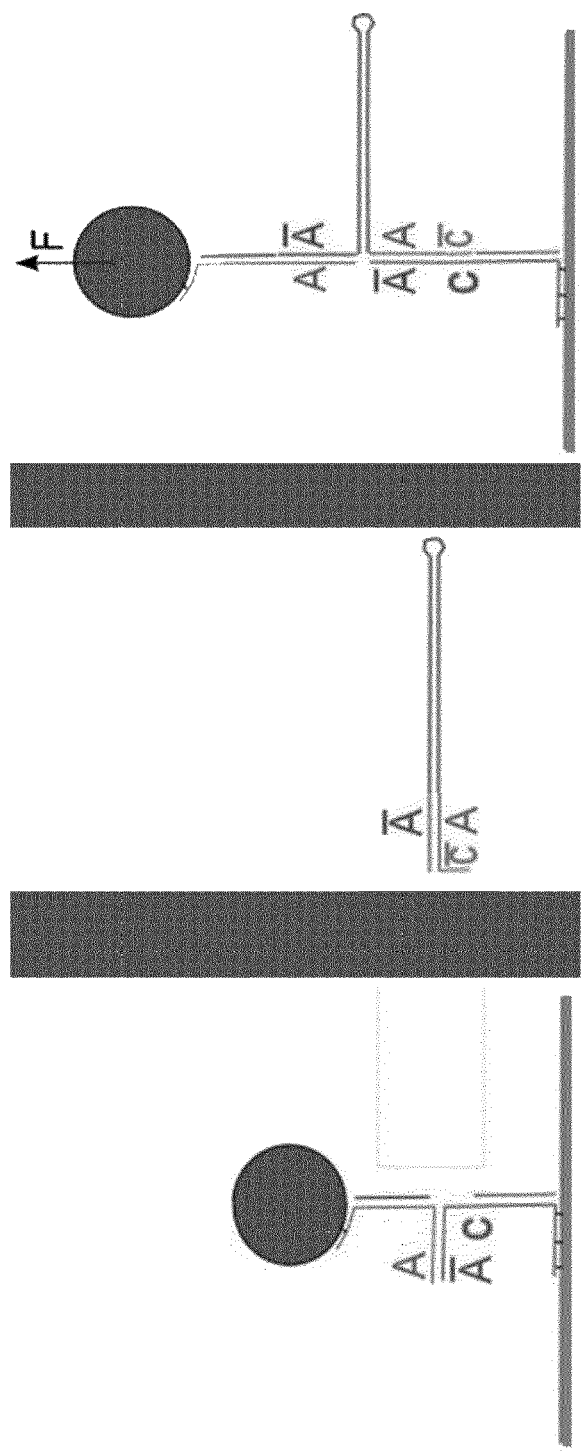

FIG. 3: Alternative strand invasion process. This example is similar to that shown in FIG. 1, with the exception that the invading hairpin has only a single flap (C') with which to bind to proto-hairpin structure affixed to the surface. The structure of the resulting strand-invaded hairpin is very similar to that in FIG. 2.

Figure 4:
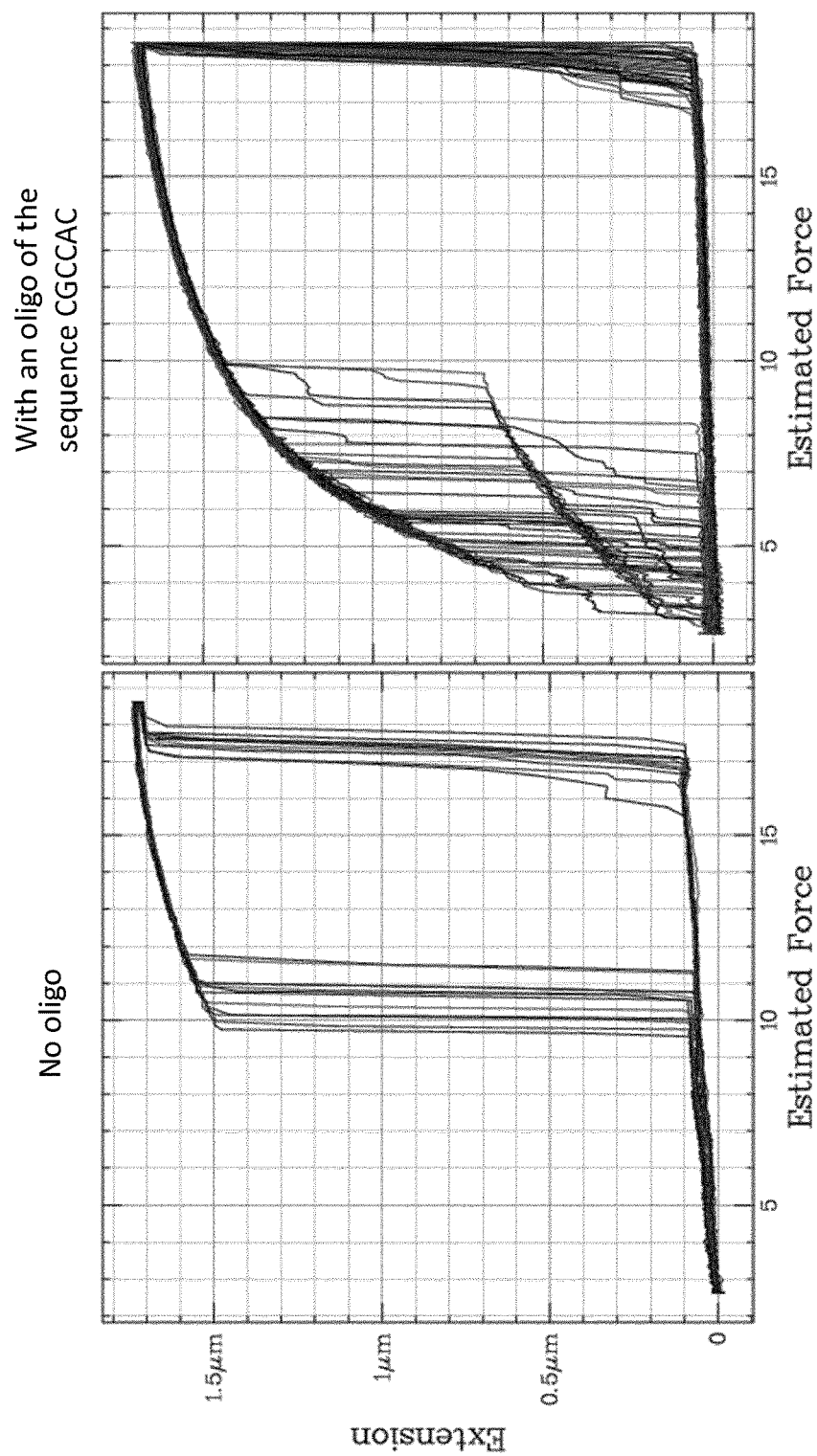

FIG. 4: Examples of fingerprints obtained with an oligonucleotide CGCCAC. A hairpin was generated with the 1.6 kb BsmBI fragment obtained from pPS002 digestion. The force on the bead was gradually increased until it reached a point where the molecule unziped. Reduction of the force caused reziping of the molecule. In the absence of any oligonucleotide, the closing was rapid (left panel). However, when the oligonucleotide was present in the flow cell and the complementary sequence of this oligonucleotide is on the hairpin, it blocked the reziping. This oligonucleotide had 3 binding positions on the hairpin, only one (at position 794 bp) is showing blockage due to the nature of the oligonucleotide. The experimental value obtained for this blockage on the particular bead was 784 bp. This oligonucleotide also blocked the reformation of the hairpin due to a blocking site located within the PS046 loop oligonucleotide, although there is a mismatch at the 5' end between the oligonucleotide and its target sequence.

Figure 5:
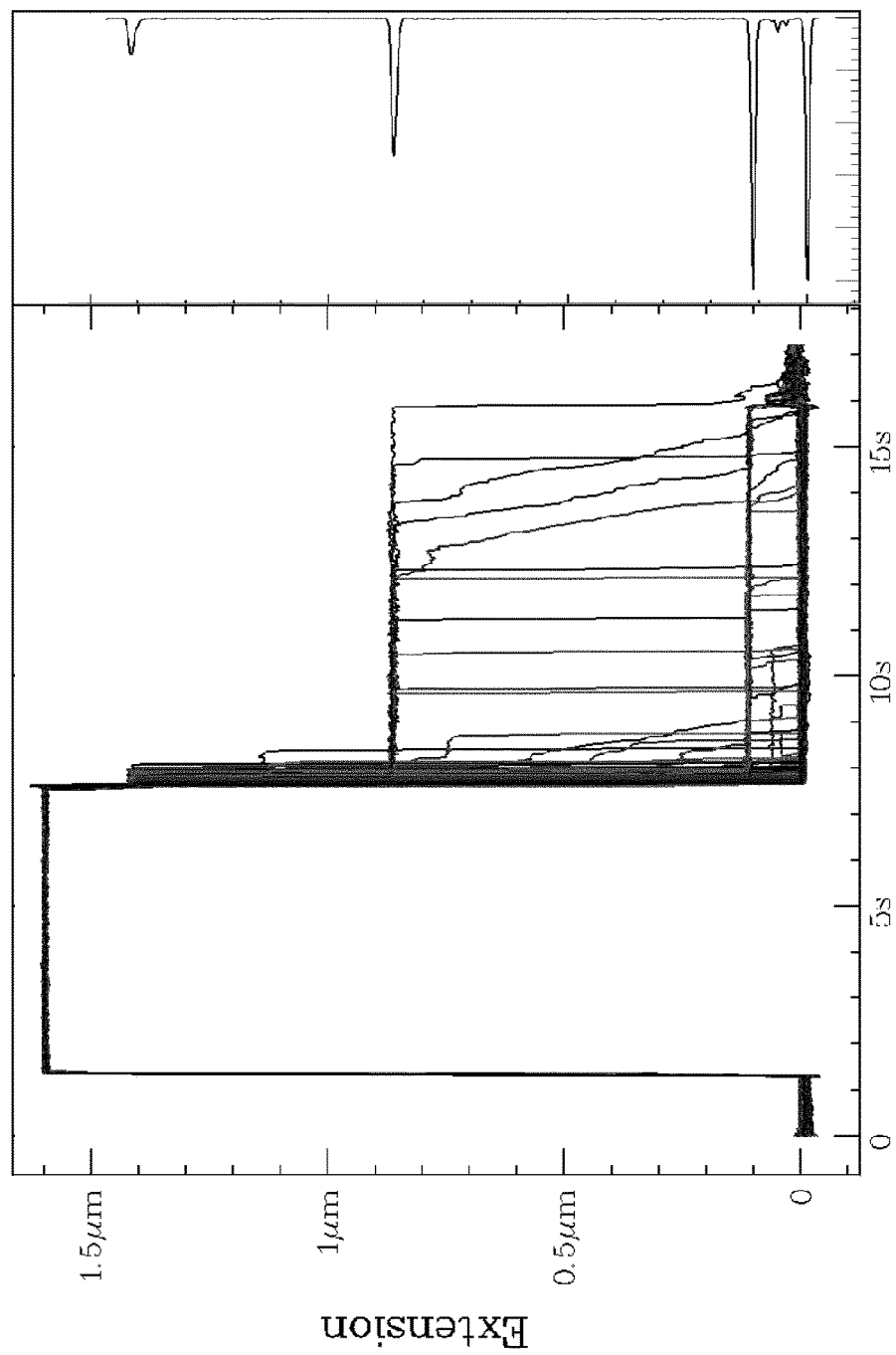

FIG. 5: Detection of the 5-methylcytosine modification. The same hairpin created through FISI with the BsmBI digested fragment from pPS003 was tested against the 5-methylcytosine modification with antibodies (the clone 33D3 monoclonal antibody was used in this experiment and is commercially available from various sources such as Merck Millipore or Sigma-Aldrich). This hairpin was predicted to contain 2 potential Dcm methylation sites at position 170 and 1046. Using the ssDNA blockage as a reference (the first one from the top), the experimental blocking position were calculated to be at 135 bp and 1035 bp. Both the oligonucleotide and the antibody confirmed that the fragment of DNA was really originating from pPS003.

EXAMPLES

Example 1

Preparation of HP1 Containing One Flap

The pPS001 vector (SEQ ID NO. 1) was used to clone a 1.5 kb KpnI fragment or a 500 bp SalI fragment from lambda genomic DNA to yield pPS002 (SEQ ID NO. 2) or pPS003 (SEQ ID NO. 3), respectively.

To create the dsDNA linker between the bead and the precursor HP1, DreamTaq DNA polymerase was used according to the manufacturer specifications. The oligonucleotides PS079 (SEQ ID NO. 6) and PS080 (SEQ ID NO. 7) were used at 500 nM concentration each and depending on the desired length of the linker, either pPS001, pPS002 or pPS003 vectors was used as template (creating a linker of either 236, 1724 or 737 base pairs, respectively).

The oligonucleotide PS080 contains a biotin at its 5' end. The oligonucleotide PS079 has a 12-carbon spacer (C12 spacer) that prevents the DNA polymerase from "copying" the 5' end of the vector, and leaves a 5', single stranded tail.

The PCR conditions were as follow:

98° C. for 3 min

58° C. for 20 sec ⎫
72° C. for 1 min ⎬ 30X
95° C. for 30 sec ⎭

72° C. for 5 min

Hold at 4° C. for ever

For the adapter between the HP1 and the surface, DreamTaq DNA polymerase was used according to the manufacturer specification with the oligonucleotides PS103 (SEQ ID NO. 8) and PS104 (SEQ ID NO. 9) on the template sequence pPS003. The same conditions as previously were used.

The resulting sequence is as follow (including the sequence added to create BsaI restriction site in green):

```
SEQ ID NO. 5:
5' attcgatcgtGGTCTCAGAATcctggtggtgagcaatggtttcaac catgtaccggatgtgttctgccatgcgctcctgaaactcaaCatcgtca tcaaacgcacgggtaatggattttttgctggcccgtggcgttgcaaat gatcgatgcatagcgattcaaacaggtgctggggcaggcTttttccat gtcgtctgccagttctgcctctttctcttcacgggcgagctgctggtag tgacgcgcccagctctgagcctcaagacGCTTGGAGACCagctagccat
3'
```

The resulting fragment was then digested with BsaI according to the manufacturer specification. On these overhangs, two different adapters are then cloned as follows:

The first of these adapters is obtained by hybridizing oligonucleotides PS101 (SEQ ID NO. 10) and PS070 (SEQ ID NO. 11). The resulting 5' overhang of PS101 is complementary to one of the fragment overhangs.

The second adapter is obtained by hybridizing oligonucleotides PS101 and PS0102 (SEQ ID NO. 12). Both ends of PS102 extend beyond PS101. One of these ends is complementary to the second overhangs of the fragment.

Specifically, the oligonucleotides PS101 and PS070 were annealed in CutSmart buffer (NEB, 1×: 50 mM Potassium Acetate, 20 mM Tris-acetate, 10 mM Magnesium Acetate, 100 µg/ml BSA, pH 7.9@25° C.) at a concentration of 10 µm each. The solution was heated at 98° C. and let cool down to room temperature on the heat block. The same procedure was performed for the oligonucleotides PS101 and PS102.

Two different adapters were thus created, that can be ligated to the BsaI digested PCR fragment directionally due to the presence of 2 different, non-palindromic, sites using T4 DNA ligase from Enzymatics according to manufacturer specification.

Once ligated, the oligonucleotide PS101 was extended using PS070 as template using Klenow exo-DNA polymerase from Enzymatics. The amount of dTTP in the reaction mix was adjusted such that dig-dUTP could be used. There was a ratio of 40% dTTP for 60% of dig-dUTP.

After purification of the final fragment on agarose gel, the molarity of both fragments was calculated. The two fragments were then mixed together at equal molarity in CutSmart buffer. The 3' end of the oligonucleotide PS102 is complementary to the 5' end of the oligonucleotide PS079, after the C12 spacer.

Once annealed, the final HP1 molecule was serially diluted and bound on MyOne paramagnetic beads functionalized with streptavidin. Since the PS080 oligonucleotide contains a biotin, the molecule will bind to the beads. The precursor HP1 was then loaded in the microfluidic chamber, the floor of the cell being functionalized with anti-digoxigenin antibodies. Due to the presence of digoxigenin on the second part of HP1, the precursor HP1 binds to the floor of the flow cell.

Preparation of HP2

For the production of HP2, the BsmBI fragment from the vector pPS002 (SEQ ID NO. 2) was obtained through digestion of the vector and purified from the gel. The resulting 1.6 kb fragment had 2 different non-palindromic ends.

The oligonucleotides PS108 (SEQ ID NO. 13) and PS109 (SEQ ID NO. 14) were mixed at equal concentration (10 µM) in CutSmart buffer and heated at 98° C. Then, the tube was slowly cooled down to room temperature to allow the 2 oligonucleotides to anneal, thus creating an adapter with the complementary overhang to the digested BsmBI fragment.

PS046 (SEQ ID NO. 15) is a self-annealing oligonucleotide, with a loop of 5 thymines and a 5' overhang enabling cloning to a BsmBI digested vector. PS046 was diluted to 10 µM, heated at 98° C. and rapidly cooled down on ice, in order to promote the formation of a small hairpin-loop structure which can be ligated to the DNA region of interest (forming HP2).

Once ligated to the BsmBI fragment, the resulting HP2 was purified onto an agarose gel and eluted into 50 µl of water. 1 µl of this HP2 was mixed with 100 µl of passivation buffer and loaded on the fluidic cell containing the HP1 attached to the surface. The magnet was brought close to the sample such that the force reached around 5 pN. The sample was left like this for 30 minutes and the force was gradually increased to 15 pN. If an ssDNA flap (C') from HP2 has hybridized to the complementary sequence C on HP1, the Holliday junction would be resolved. In case there is no HP2 attached to HP1, the bead would fly away. Once resolved, the hairpin can be interrogated with either oligonucleotides or any other binding molecules like antibodies or proteins.

Example 2

Preparation of HP1 Molecule Containing Two Flaps.

For this version, the hairpin of interest contains two ssDNA stretches that can bind on either side of the fork.

For the 2 flap strategy, the procedure is basically the same except that the oligonucleotides used are slightly different.

For the biotin-Space linker, there is no change. PS079 and PS080 were used on pPS003 vector For the dig linker, PS102 was replaced by the oligonucleotide PS115 (SEQ ID NO. 16). The latter was then annealed with PS101 to create the adapter to be ligated with the BsaI digested PCR fragment obtained with PS103-PS104. The second adapter, PS101-PS070 was unchanged. The dig-tail was then synthesised as previously described.

Both fragments were purified on agarose gel and mixed at equal amount to form the HP1. Then, they were serially diluted and bound to MyOne paramagnetic beads coated with streptavidin.

For making the HP2, the PS107-PS108 adapter were replaced with the adapter composed of PS116 (SEQ ID NO. 17)-PS118 (SEQ ID NO. 18) to make the two flap HP2. They were mixed in CutSmart buffer at 10 μM, heated at 98° C. and slowly cooled to room temperature. They were finally ligated as well as the loop PS046 to the BsmBI fragment from pPS002 vector.

The final fragment was purified on agarose gel and 1 μl of the resulting eluate was loaded inside the flow cell containing the HP1 precursor. The same procedure as previously was applied.

The invention claimed is:

1. A method for preparing a hairpin nucleic acid comprising a sequence of interest, said method comprising the steps of:

(a) providing a nucleic acid HP1, said nucleic acid HP1 comprising:
  a first end bound to a first surface;
  a single-stranded sequence A linked to said first end,
  a single-stranded sequence A' hybridized to said sequence A, wherein said sequence A and said sequence A' are not covalently linked; and form a double stranded region compromising the sequence A and the sequence A';
  a single-stranded sequence C linked to said sequence A';
  a second end linked to said sequence C, wherein said second end is bound to a second surface;
  wherein one of the first surface and the second surface is a movable surface and the first surface and the second surface are different surfaces;

b) providing at least one nucleic acid HP2, said nucleic acid HP2 comprising:
  a double-stranded region comprising the sequence of interest,
  a loop linked to a first end of said double-stranded region that links the two strands of said double-stranded region,
  a single-stranded region having the sequence A linked to a first strand of a second end of said double-stranded region, said single-stranded region having the sequence A being linked to a single-stranded sequence C', the sequence C' being complementary to the sequence C;
  a single-stranded polynucleotide having the sequence A' linked to a second strand of the second end of said double-stranded region wherein the sequence A hybridizes to the sequence A' and form a double stranded region comprising the sequence A and the sequence A';

c) denaturing said nucleic acid HP1 from step a) in the presence of said nucleic acid HP2 from step b) by moving one surface of the first surface and the second surface away from another surface of the first surface and the second surface by applying a tension of at least 3 pN to the moveable surface, such that said double stranded region comprising the sequence A and the sequence A' of said nucleic acid HP1 are completely denatured; and d) obtaining said hairpin nucleic acid, wherein said hairpin nucleic acid is formed by hybridizing said nucleic acid HP1 to said nucleic acid HP2 in the presence of the tension.

2. The method of claim 1, wherein:

said sequence A of said nucleic acid HP1 is linked to a single-stranded sequence D, said sequence D being located between said sequence A and said first surface and said sequence A linked to said first end bound to the first surface by said sequence D; and said sequence A' of said nucleic acid HP2 is linked to a single-stranded region having sequence D', wherein the sequence D' is complementary to the sequence D of said nucleic acid HP1.

3. The method of claim 2, wherein each of the sequence D and the sequence D' comprises at least 10 nucleotides.

4. The method of claim 2, wherein each of the sequence D and the sequence D' comprises at least 12 nucleotides.

5. The method of claim 2, wherein each of the sequence D and the sequence D' comprises at least 13 nucleotides.

6. The method of claim 1, wherein the tension of at least 3 pN is a tension of at least 4 pN.

7. The method of claim 1, wherein more than one molecule of said nucleic acid HP1 is attached to one of the first surface and the second surface.

8. The method of claim 1, wherein said at least one nucleic acid HP2 comprises a plurality of distinct nucleic acid molecules.

9. The method of claim 1, wherein each of the sequence A and the sequence A' comprises at least 30 nucleotides.

10. The method of claim 1, wherein each of the sequence C and the sequence C' comprises at least 10 nucleotides.

11. The method of claim 1, further comprising:

e) completely denaturing the hairpin structure in the hairpin nucleic acid by moving one surface of the first surface and the second surface away from another surface of the first surface and the second surface and obtaining a nucleic acid molecule without the hairpin structure;

f) measuring the distance ($Z_{high}$) between the two ends of the nucleic acid molecule without the hairpin structure obtained in step e);

g) hybridizing a single-stranded nucleic acid molecule with said nucleic acid molecule without the hairpin structure obtained in step e) and generating a complex;

h) renaturing said hairpin structure of said complex from step g);

i) detecting a blockage of the renaturation of said hairpin structure of said complex, wherein said blockage is caused by said single-stranded nucleic acid molecule of said complex; and j) determining the position of said blockage with respect to one end of the hairpin nucleic acid, said determination comprising the steps of:

measuring distance (z) between the two ends of the hairpin nucleic acid which are attached to the first surface and the second surface during the period of said blockage, comparing z and $Z_{high}$, and determining the position of the blockage with respect to one end of the hairpin nucleic acid.

12. The method of claim 1, further comprising:

e) completely denaturing the hairpin structure in the hairpin nucleic acid by moving one surface of the first surface and the second surface away from another surface of the first surface and the second surface and obtaining a nucleic acid molecule without the hairpin structure;

f) measuring the distance ($Z_{high}$) between the two ends of the nucleic acid molecule without the hairpin structure obtained in step e);

g) hybridizing a single-stranded nucleic acid molecule with said nucleic acid molecule without the hairpin structure obtained in step e) and generating a complex;

h) renaturing said hairpin structure of said complex from step g);

i) detecting a blockage of the renaturation of said hairpin structure of said complex, wherein said blockage is caused by said single-stranded nucleic acid molecule of said complex;

j) determining the position of said blockage with respect to one end of the hairpin nucleic acid, said determination comprising the steps of:

measuring distance (z) between the two ends of the hairpin nucleic acid which are attached to the first surface and the second surface during the period of said blockage, comparing z and $Z_{high}$, and determining the position of the blockage with respect to one end of the hairpin nucleic acid; and k) determining the duration of said blockage.

13. The method of claim 1, further comprising:

e) completely denaturing the hairpin structure in the hairpin nucleic acid by moving one surface of the first surface and the second surface away from another surface of the first surface and the second surface and obtaining a nucleic acid molecule without the hairpin structure;

f) measuring the distance ($Z_{high}$) between the two ends of the nucleic acid molecule without the hairpin structure obtained in step e);

g) contacting a single-stranded nucleic acid-binding protein with said nucleic acid molecule without the hairpin structure obtained in step e) and generating a complex;

h) renaturing said hairpin structure of said complex from step g) in the presence of said protein;

i) detecting a blockage of the renaturation of the hairpin structure, wherein said blockage is caused by binding said protein to a single-stranded region of said nucleic acid molecule without the hairpin structure;

j) determining the position of said blockage with respect to one end of the hairpin nucleic acid, said determination comprising the steps of:

measuring distance (z) between the two ends of the hairpin nucleic acid which are attached to the first surface and the second surface during the period of said blockage, comparing z and $Z_{high}$, and determining the position of the blockage with respect to one end of the hairpin nucleic acid; and k) determining the duration of said blockage.

14. The method of claim 1, further comprising:

e) completely denaturing the hairpin structure in the hairpin nucleic acid by moving one surface of the first surface and the second surface away from another surface of the first surface and the second surface and obtaining a nucleic acid molecule without the hairpin structure;

f) measuring the distance ($Z_{high}$) between the two ends of the nucleic acid molecule without the hairpin structure obtained in step e);

g) contacting a double-stranded nucleic acid-binding protein and a single-stranded nucleic acid molecule with said nucleic acid molecule without the hairpin structure obtained in step e) and generating a complex, wherein the single-stranded nucleic acid molecule hybridizes to said nucleic acid molecule without the hairpin structure;

h) renaturing said hairpin structure of said complex from step g) in the presence of said protein;

i) detecting a blockage of the renaturation of the hairpin structure, wherein said blockage is caused by binding said protein to a double-stranded region in the complex formed by the single-stranded nucleic acid molecule and a single stranded region generated by complete denaturation of the hairpin structure;

j) determining the position of said blockage with respect to one end of the hairpin nucleic acid, said determination comprising the steps of:

measuring distance (z) between the two ends of the hairpin nucleic acid which are attached to the first surface and the second surface during the period of said blockage, comparing z and $Z_{high}$, and determining the position of the blockage with respect to one end of the hairpin nucleic acid; and k) determining the duration of said blockage.

15. The method of claim 1, wherein the tension of at least 3 pN is a tension of at least 5 pN.

16. The method of claim 1, wherein the tension of at least 3 pN is a tension of at least 6 pN.

17. The method of claim 1, wherein each of the sequence A and the sequence A' comprises at least 35 nucleotides.

18. The method of claim 1, wherein each of the sequence C and the sequence C' comprises at least 12 nucleotides.

* * * * *

SEQUENCE LISTING

<160> NUMBER OF SEQ ID NOS: 18

<210> SEQ ID NO 1
<211> LENGTH: 2966
<212> TYPE: DNA
<213> ORGANISM: Artificial
<220> FEATURE:
<223> OTHER INFORMATION: pSP01

<400> SEQUENCE: 1

```
ctaaattgta agcgttaata ttttgttaaa attcgcgtta aattttttgtt aaatcagctc      60 atttttttaac caataggccg aaatcggcaa atcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgaat tgtaatacga ctcactatag ggcgaatgga gacgagctcc     660
accgcggtgg cggccgctct agaactagtg gatccccgg gctgcaggaa ttcgatatca     720
agcttatcga taccgtcgac ctcgaggggg ggcccggtac cgtctcagct tttgttccct     780
ttagtgaggg ttaatttcga gcttggcgta atcatggtca tagctgtttc ctgtgtgaaa     840
ttgttatccg ctcacaattc cacacaacat acgagccgga agcataaagt gtaaagcctg     900
gggtgcctaa tgagtgagct aactcacatt aattgcgttg cgctcactgc ccgctttcca     960
gtcgggaaac ctgtcgtgcc agctgcatta atgaatcggc caacgcgcgg ggagaggcgg    1020
tttgcgtatt gggcgctctt ccgcttcctc gctcactgac tcgctgcgct cggtcgttcg    1080
gctgcggcga gcggtatcag ctcactcaaa ggcggtaata cggttatcca cagaatcagg    1140
ggataacgca ggaaagaaca tgtgagcaaa aggccagcaa aaggccagga accgtaaaaa    1200
ggccgcgttg ctggcgtttt tccataggct ccgcccccct gacgagcatc acaaaaatcg    1260
acgctcaagt cagaggtggc gaaacccgac aggactataa agataccagg cgtttccccc    1320
tggaagctcc ctcgtgcgct ctcctgttcc gaccctgccg cttaccggat acctgtccgc    1380
ctttctccct tcgggaagcg tggcgctttc tcatagctca cgctgtaggt atctcagttc    1440
ggtgtaggtc gttcgctcca agctgggctg tgtgcacgaa ccccccgttc agcccgaccg    1500
ctgcgcctta tccggtaact atcgtcttga gtccaacccg gtaagacacg acttatcgcc    1560
actggcagca gccactggta acaggattag cagagcgagg tatgtaggcg gtgctacaga    1620
```

| | |
|---|---:|
| gttcttgaag tggtggccta actacggcta cactagaagg acagtatttg gtatctgcgc | 1680 |
| tctgctgaag ccagttacct tcggaaaaag agttggtagc tcttgatccg gcaaacaaac | 1740 |
| caccgctggt agcggtggtt tttttgtttg caagcagcag attacgcgca gaaaaaaagg | 1800 |
| atctcaagaa gatcctttga tcttttctac ggggtctgac gctcagtgga acgaaaactc | 1860 |
| acgttaaggg attttggtca tgagattatc aaaaaggatc ttcacctaga tccttttaaa | 1920 |
| ttaaaaatga agttttaaat caatctaaag tatatatgag taaacttggt ctgacagtta | 1980 |
| ccaatgctta atcagtgagg cacctatctc agcgatctgt ctatttcgtt catccatagt | 2040 |
| tgcctgactc cccgtcgtgt agataactac gatacgggag gcttaccat ctggccccag | 2100 |
| tgctgcaatg ataccgcgag acccacgctc accggctcca gatttatcag caataaacca | 2160 |
| gccagccgga agggccgagc gcagaagtgg tcctgcaact ttatccgcct ccatccagtc | 2220 |
| tattaattgt tgccgggaag ctagagtaag tagttcgcca gttaatagtt tgcgcaacgt | 2280 |
| tgttgccatt gctacaggca tcgtggtgtc acgctcgtcg tttggtatgg cttcattcag | 2340 |
| ctccggttcc caacgatcaa ggcgagttac atgatccccc atgttgtgca aaaaagcggt | 2400 |
| tagctccttc ggtcctccga tcgttgtcag aagtaagttg gccgcagtgt tatcactcat | 2460 |
| ggttatggca gcactgcata attctcttac tgtcatgcca tccgtaagat gcttttctgt | 2520 |
| gactggtgag tactcaacca agtcattctg agaatagtgt atgcggcgac cgagttgctc | 2580 |
| ttgcccggcg tcaatacggg ataataccgc gccacatagc agaactttaa aagtgctcat | 2640 |
| cattggaaaa cgttcttcgg ggcgaaaact ctcaaggatc ttaccgctgt tgagatccag | 2700 |
| ttcgatgtaa cccactcgtg cacccaactg atcttcagca tcttttactt tcaccagcgt | 2760 |
| ttctgggtga gcaaaaacag gaaggcaaaa tgccgcaaaa aagggaataa gggcgacacg | 2820 |
| gaaatgttga atactcatac tcttcctttt tcaatattat tgaagcattt atcagggtta | 2880 |
| ttgtctcatg agcggataca tatttgaatg tatttagaaa aataaacaaa taggggttcc | 2940 |
| gcgcacattt ccccgaaaag tgccac | 2966 |

<210> SEQ ID NO 2
<211> LENGTH: 4469
<212> TYPE: DNA
<213> ORGANISM: Artificial
<220> FEATURE:
<223> OTHER INFORMATION: pPS02

<400> SEQUENCE: 2

| | |
|---|---:|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt ttttttgggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgaat tgtaatacga ctcactatag ggcgaatgga gacgagctcc | 660 |

```
accgcggtgg cggccgctct agaactagtg gatcccccgg gctgcaggaa ttcgatatca    720
agcttatcga taccgtcgac ctcgaggggg ggcccggtac cgcgctgata agcctggttg    780
acggaagtgg caatccggtc agcgtggagg ttcagtccgt caccgacggc gtgaaggtaa    840
aagtgagccg tgttcctgac ggtgttgctg aatacagcgt atgggagctg aagctgccga    900
cgctgcgcca gcgactgttc cgctgcgtga gtatccgtga aacgacgac ggcacgtatg     960 ccatcaccgc cgtgcagcat gtgccggaaa aagaggccat cgtggataac ggggcgcact   1020
ttgacggcga acagagtggc acggtgaatg gtgtcacgcc gccagcggtg cagcacctga   1080
ccgcagaagt cactgcagac agcggggaat atcaggtgct ggcgcgatgg gacacaccga   1140
aggtggtgaa gggcgtgagt ttcctgctcc gtctgaccgt aacagcggac gacggcagtg   1200
agcggctggt cagcacggcc cggacgacgg aaaccacata ccgcttcacg caactggcgc   1260
tggggaacta caggctgaca gtccggcgg taaatgcgtg ggggcagcag ggcgatccgg    1320
cgtcggtatc gttccggatt gccgcaccgg cagcaccgtc gaggattgag ctgacgccgg   1380
gctattttca gataaccgcc acgccgcatc ttgccgttta tgacccgacg gtacagtttg   1440
agttctggtt ctcggaaaag cagattgcgg atatcagaca ggttgaaacc agcacgcgtt   1500
atcttggtac ggcgctgtac tggatagccg ccagtatcaa tatcaaaccg gccatgatt    1560 attacttta tatccgcagt gtgaacaccg ttggcaaatc ggcattcgtg gaggccgtcg    1620
gtcgggcgag cgatgatgcg gaaggttacc tggattttt caaaggcaag ataaccgaat    1680
cccatctcgg caaggagctg ctggaaaaag tcgagctgac ggaggataac gccagcagac   1740
tggaggagtt ttcgaaagag tggaaggatg ccagtgataa gtggaatgcc atgtgggctg   1800
tcaaaattga gcagaccaaa gacggcaaac attatgtcgc gggtattggc ctcagcatgg   1860
aggacacgga ggaaggcaaa ctgagccagt ttctggttgc cgccaatcgt atcgcattta   1920
ttgacccggc aaacgggaat gaaacgccga tgtttgtggc gcagggcaac cagatattca   1980
tgaacgacgt gttcctgaag cgcctgacgg cccccaccat taccagcggc ggcaatcctc   2040
cggccttttc cctgacaccg gacggaaagc tgaccgctaa aaatgcggat atcagtggca   2100
gtgtgaatgc gaactccggg acgctcagta atgtgacgat agctgaaaac tgtacgataa   2160
acggtacgct gagggcggaa aaaatcgtcg gggacattgt aaaggcggcg agcgcggctt   2220
ttccgcgcca gcgtgaaagc agtgtggact ggccgtcagg taccgtctca gcttttgttc   2280
cctttagtga gggttaattt cgagcttggc gtaatcatgg tcatagctgt ttcctgtgtg   2340
aaattgttat ccgctcacaa ttccacacaa catacgagcc ggaagcataa agtgtaaagc   2400
ctggggtgcc taatgagtga gctaactcac attaattgcg ttgcgctcac tgcccgcttt   2460
ccagtcggga aacctgtcgt gccagctgca ttaatgaatc ggccaacgcg cggggagagg   2520
cggtttgcgt attgggcgct cttccgcttc ctcgctcact gactcgctgc gctcggtcgt   2580
tcggctgcgg cgagcggtat cagctcactc aaaggcggta atacggttat ccacagaatc   2640
aggggataac gcaggaaaga acatgtgagc aaaaggccag caaaaggcca ggaaccgtaa   2700
aaaggccgcg ttgctggcgt ttttccatag gctccgcccc cctgacgagc atcacaaaaa   2760
tcgacgctca agtcagaggt ggcgaaaccc gacaggacta taaagatacc aggcgtttcc   2820
ccctggaagc tccctcgtgc gctctcctgt tccgaccctg ccgcttaccg gatacctgtc   2880
cgcctttctc ccttcgggaa gcgtggcgct ttctcatagc tcacgctgta ggtatctcag   2940
ttcggtgtag gtcgttcgct ccaagctggg ctgtgtgcac gaaccccccg ttcagcccga   3000
ccgctgcgcc ttatccggta actatcgtct tgagtccaac ccggtaagac acgacttatc   3060
```

| | | | | |
|---|---|---|---|---|
| gccactggca | gcagccactg | gtaacaggat | tagcagagcg | aggtatgtag gcggtgctac | 3120 |
| agagttcttg | aagtggtggc | ctaactacgg | ctacactaga | aggacagtat ttggtatctg | 3180 |
| cgctctgctg | aagccagtta | ccttcggaaa | aagagttggt | agctcttgat ccggcaaaca | 3240 |
| aaccaccgct | ggtagcggtg | gttttttttgt | ttgcaagcag | cagattacgc gcagaaaaaa | 3300 |
| aggatctcaa | gaagatcctt | tgatcttttc | tacggggtct | gacgctcagt ggaacgaaaa | 3360 |
| ctcacgttaa | gggattttgg | tcatgagatt | atcaaaaagg | atcttcacct agatcctttt | 3420 |
| aaattaaaaa | tgaagtttta | aatcaatcta | agtatatat | gagtaaactt ggtctgacag | 3480 |
| ttaccaatgc | ttaatcagtg | aggcacctat | ctcagcgatc | tgtctatttc gttcatccat | 3540 |
| agttgcctga | ctccccgtcg | tgtagataac | tacgatacgg | gagggcttac catctggccc | 3600 |
| cagtgctgca | atgataccgc | gagacccacg | ctcaccggct | ccagatttat cagcaataaa | 3660 |
| ccagccagcc | ggaagggccg | agcgcagaag | tggtcctgca | actttatccg cctccatcca | 3720 |
| gtctattaat | tgttgccggg | aagctagagt | aagtagttcg | ccagttaata gtttgcgcaa | 3780 |
| cgttgttgcc | attgctacag | gcatcgtggt | gtcacgctcg | tcgtttggta tggcttcatt | 3840 |
| cagctccggt | tcccaacgat | caaggcgagt | tacatgatcc | cccatgttgt gcaaaaaagc | 3900 |
| ggttagctcc | ttcggtcctc | cgatcgttgt | cagaagtaag | ttggccgcag tgttatcact | 3960 |
| catggttatg | gcagcactgc | ataattctct | tactgtcatg | ccatccgtaa gatgcttttc | 4020 |
| tgtgactggt | gagtactcaa | ccaagtcatt | ctgagaatag | tgtatgcggc gaccgagttg | 4080 |
| ctcttgcccg | gcgtcaatac | gggataatac | cgcgccacat | agcagaactt taaaagtgct | 4140 |
| catcattgga | aaacgttctt | cggggcgaaa | actctcaagg | atcttaccgc tgttgagatc | 4200 |
| cagttcgatg | taacccactc | gtgcacccaa | ctgatcttca | gcatctttta ctttcaccag | 4260 |
| cgtttctggg | tgagcaaaaa | caggaaggca | aaatgccgca | aaaagggaa taaggcgac | 4320 |
| acggaaatgt | tgaatactca | tactcttcct | ttttcaatat | tattgaagca tttatcaggg | 4380 |
| ttattgtctc | atgagcggat | acatatttga | atgtatttag | aaaaataaac aaatagggt | 4440 |
| tccgcgcaca | tttccccgaa | aagtgccac | | | 4469 |

<210> SEQ ID NO 3
<211> LENGTH: 3467
<212> TYPE: DNA
<213> ORGANISM: Artificial
<220> FEATURE:
<223> OTHER INFORMATION: pSP03

<400> SEQUENCE: 3

| | | | | |
|---|---|---|---|---|
| ctaaattgta | agcgttaata | ttttgttaaa | attcgcgtta | aatttttgtt aaatcagctc | 60 |
| attttttaac | caataggccg | aaatcggcaa | aatcccttat | aaatcaaaag aatagaccga | 120 |
| gatagggttg | agtgttgttc | cagtttggaa | caagagtcca | ctattaaaga acgtggactc | 180 |
| caacgtcaaa | gggcgaaaaa | ccgtctatca | gggcgatggc | ccactacgtg aaccatcacc | 240 |
| ctaatcaagt | tttttggggt | cgaggtgccg | taaagcacta | aatcggaacc ctaaagggag | 300 |
| cccccgattt | agagcttgac | ggggaaagcc | ggcgaacgtg | gcgagaaagg aagggaagaa | 360 |
| agcgaaagga | gcgggcgcta | gggcgctggc | aagtgtagcg | gtcacgctgc gcgtaaccac | 420 |
| cacacccgcc | gcgcttaatg | cgccgctaca | gggcgcgtcc | cattcgccat tcaggctgcg | 480 |
| caactgttgg | gaagggcgat | cggtgcgggc | ctcttcgcta | ttacgccagc tggcgaaagg | 540 |
| gggatgtgct | gcaaggcgat | taagttgggt | aacgccaggg | ttttcccagt cacgacgttg | 600 |

-continued

```
taaaacgacg gccagtgaat tgtaatacga ctcactatag ggcgaatgga gacgagctcc      660
accgcgtgg  cggccgctct agaactagtg gatccccccgg gctgcaggaa ttcgatatca     720
agcttatcga taccgtcgac agaatccatg ccgacacgtt cagccagctt cccagccagc      780
gttgcgagtg cagtactcat tcgttttata cctctgaatc aatatcaacc tggtggtgag      840
caatggtttc aaccatgtac cggatgtgtt ctgccatgcg ctcctgaaac tcaacatcgt      900
catcaaacgc acgggtaatg gatttttgc  tggccccgtg gcgttgcaaa tgatcgatgc      960
atagcgattc aaacaggtgc tggggcaggc cttttccat  gtcgtctgcc agttctgcct     1020
ctttctcttc acgggcgagc tgctggtagt gacgcgccca gctctgagcc tcaagacgat     1080
cctgaatgta ataagcgttc atggctgaac tcctgaaata gctgtgaaaa tatcgcccgc     1140
gaaatgccgg gctgattagg aaaacaggaa aggggttag  tgaatgcttt tgcttgatct     1200
cagtttcagt attaatatcc attttttata agcgtcgacc ctcgagggg  ggcccgggta     1260
ccgtctcagc ttttgttccc tttagtgagg gttaatttcg agcttggcgt aatcatggtc     1320
atagctgttt cctgtgtgaa attgttatcc gctcacaatt ccacacaaca tacgagccgg     1380
aagcataaag tgtaaagcct ggggtgccta atgagtgagc taactcacat taattgcgtt     1440
gcgctcactg cccgctttcc agtcgggaaa cctgtcgtgc cagctgcatt aatgaatcgg     1500
ccaacgcgcg gggagaggcg gtttgcgtat tgggcgctct tccgcttcct cgctcactga     1560
ctcgctgcgc tcggtcgttc ggctgcggcg agcggtatca gctcactcaa aggcggtaat     1620
acggttatcc acagaatcag gggataacgc aggaaagaac atgtgagcaa aaggccagca     1680
aaaggccagg aaccgtaaaa aggccgcgtt gctggcgttt ttccataggc tccgcccccc     1740
tgacgagcat cacaaaaatc gacgctcaag tcagaggtgg cgaaacccga caggactata     1800
aagataccag gcgtttcccc ctggaagctc cctcgtgcgc tctcctgttc cgaccctgcc     1860
gcttaccgga tacctgtccg cctttctccc ttcgggaagc gtggcgcttt ctcatagctc     1920
acgctgtagg tatctcagtt cggtgtaggt cgttcgctcc aagctgggct gtgtgcacga     1980
accccccgtt cagcccgacc gctgcgcctt atccggtaac tatcgtcttg agtccaaccc     2040
ggtaagacac gacttatcgc cactggcagc agccactggt aacaggatta gcagagcgag     2100
gtatgtaggc ggtgctacag agttcttgaa gtggtggcct aactacggct acactagaag     2160
gacagtattt ggtatctgcg ctctgctgaa gccagttacc ttcggaaaaa gagttggtag     2220
ctcttgatcc ggcaaacaaa ccaccgctgg tagcggtggt ttttttgttt gcaagcagca     2280
gattacgcgc agaaaaaaag gatctcaaga agatcctttg atcttttcta cggggtctga     2340
cgctcagtgg aacgaaaact cacgttaagg gattttggtc atgagattat caaaaaggat     2400
cttcacctag atccttttaa attaaaaatg aagttttaaa tcaatctaaa gtatatatga     2460
gtaaacttgg tctgacagtt accaatgctt aatcagtgag gcacctatct cagcgatctg     2520
tctatttcgt tcatccatag ttgcctgact ccccgtcgtg tagataacta cgatacggga     2580
gggcttacca tctggcccca gtgctgcaat gataccgcga acccacgct  caccggctcc     2640
agatttatca gcaataaacc agccagccgg aagggccgag cgcagaagtg gtcctgcaac     2700
tttatccgcc tccatccagt ctattaattg ttgccgggaa gctagagtaa gtagttcgcc     2760
agttaatagt ttgcgcaacg ttgttgccat tgctacaggc atcgtggtgt cacgctcgtc     2820
gtttggtatg gcttcattca gctccggttc ccaacgatca aggcgagtta catgatcccc     2880
catgttgtgc aaaaaagcgg ttagctcctt cggtcctccg atcgttgtca gaagtaagtt     2940
ggccgcagtg ttatcactca tggttatggc agcactgcat aattctctta ctgtcatgcc     3000
```

| | |
|---|---:|
| atccgtaaga tgcttttctg tgactggtga gtactcaacc aagtcattct gagaatagtg | 3060 |
| tatgcggcga ccgagttgct cttgcccggc gtcaatacgg gataataccg cgccacatag | 3120 |
| cagaacttta aaagtgctca tcattggaaa acgttcttcg gggcgaaaac tctcaaggat | 3180 |
| cttaccgctg ttgagatcca gttcgatgta acccactcgt gcacccaact gatcttcagc | 3240 |
| atcttttact ttcaccagcg tttctgggtg agcaaaaaca ggaaggcaaa atgccgcaaa | 3300 |
| aaagggaata agggcgacac ggaaatgttg aatactcata ctcttccttt ttcaatatta | 3360 |
| ttgaagcatt tatcagggtt attgtctcat gagcggatac atatttgaat gtatttagaa | 3420 |
| aaataaacaa ataggggttc cgcgcacatt tccccgaaaa gtgccac | 3467 |

```
<210> SEQ ID NO 4
<211> LENGTH: 3848
<212> TYPE: DNA
<213> ORGANISM: Artificial
<220> FEATURE:
<223> OTHER INFORMATION: pSP06

<400> SEQUENCE: 4
```

| | |
|---|---:|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta aatcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgaat tgtaatacga ctcactatag gcgaatgga gacgagctca | 660 |
| ggccttagag tcaagactac agtagatact aatgactgac agtaccatca gcatctctat | 720 |
| atgtaacaga gtcttagaac tgtagtactc atgtcatgat cagatccatc ttgatgtact | 780 |
| gtcagactat cctcataagt ctagtgagta ctgaagatac atagctcaga tctgatcata | 840 |
| cacgacagga gtagaagtat acactgaagt agatagatcg attgactatg accatgctat | 900 |
| gactgactgc tactattcta gagtgacagt attactaagt acgagcatct aacaagatga | 960 |
| acctgacaga cactgacata gcgattatca tagctagtca ctctgacgta tctcagtcta | 1020 |
| acatcagcac atgaatgtat gactacagtt actatcaagt acactctgag tcagcatcat | 1080 |
| cagtagatcg atcagtacag tatctaggac atgactactt gagtgagaga atcttctact | 1140 |
| atctgtagtc agcttcgtaa cactctgatg tcatcttaat gctatgattg tctacttgat | 1200 |
| cgactactag ataactatag ttcagcagta cgaattgcag cgagaccatc ccaggctcgc | 1260 |
| atggtctcac agcgatccga tatcactagt gtacactgat cacatgtact agaataccag | 1320 |
| gttactatga atgagtacga tagctatcag atgtactact actagataca cgttgtcatt | 1380 |
| agtcactagg atcagtacta cttcgatcac tagatgttac agtcagagtc ctcttagatt | 1440 |
| gatacagtat actacatgac atattagtcc agtacataca gacatgattc acgtgacatt | 1500 |
| atgagtacca tcattcagat cagtcaccat tactgtgaga tactagctag agtagactac | 1560 |

-continued

| | |
|---|---|
| tgatcgacta catgtcagtc tcagtacgtt gtatcatagt cacattacat catgtatgct | 1620 |
| attcagattg agttaacggt accgtctcag ctttgttcc ctttagtgag ggttaatttc | 1680 |
| gagcttggcg taatcatggt catagctgtt tcctgtgtga aattgttatc cgctcacaat | 1740 |
| tccacacaac atacgagccg gaagcataaa gtgtaaagcc tggggtgcct aatgagtgag | 1800 |
| ctaactcaca ttaattgcgt tgcgctcact gcccgctttc cagtcgggaa acctgtcgtg | 1860 |
| ccagctgcat taatgaatcg gccaacgcgc ggggagaggc ggtttgcgta ttgggcgctc | 1920 |
| ttccgcttcc tcgctcactg actcgctgcg ctcggtcgtt cggctgcggc gagcggtatc | 1980 |
| agctcactca aaggcggtaa tacggttatc cacagaatca ggggataacg caggaaagaa | 2040 |
| catgtgagca aaaggccagc aaaaggccag gaaccgtaaa aaggccgcgt tgctggcgtt | 2100 |
| tttccatagg ctccgccccc ctgacgagca tcacaaaaat cgacgctcaa gtcagaggtg | 2160 |
| gcgaaacccg acaggactat aaagatacca ggcgtttccc cctggaagct ccctcgtgcg | 2220 |
| ctctcctgtt ccgaccctgc cgcttaccgg atacctgtcc gcctttctcc cttcgggaag | 2280 |
| cgtggcgctt tctcatagct cacgctgtag gtatctcagt tcggtgtagg tcgttcgctc | 2340 |
| caagctgggc tgtgtgcacg aaccccccgt tcagcccgac cgctgcgcct tatccggtaa | 2400 |
| ctatcgtctt gagtccaacc cggtaagaca cgacttatcg ccactggcag cagccactgg | 2460 |
| taacaggatt agcagagcga ggtatgtagg cggtgctaca gagttcttga agtggtggcc | 2520 |
| taactacggc tacactagaa ggacagtatt tggtatctgc gctctgctga gccagttac | 2580 |
| cttcggaaaa agagttggta gctcttgatc cggcaaacaa accaccgctg gtagcggtgg | 2640 |
| tttttttgtt tgcaagcagc agattacgcg cagaaaaaaa ggatctcaag aagatccttt | 2700 |
| gatcttttct acggggtctg acgctcagtg gaacgaaaac tcacgttaag ggattttggt | 2760 |
| catgagatta tcaaaaagga tcttcaccta gatcctttta aattaaaaat gaagttttaa | 2820 |
| atcaatctaa agtatatatg agtaaacttg gtctgacagt taccaatgct taatcagtga | 2880 |
| ggcacctatc tcagcgatct gtctatttcg ttcatccata gttgcctgac tccccgtcgt | 2940 |
| gtagataact acgatacggg agggcttacc atctggcccc agtgctgcaa tgataccgcg | 3000 |
| agacccacgc tcaccggctc cagatttatc agcaataaac cagccagccg gaagggccga | 3060 |
| gcgcagaagt ggtcctgcaa ctttatccgc ctccatccag tctattaatt gttgccggga | 3120 |
| agctagagta agtagttcgc cagttaatag tttgcgcaac gttgttgcca ttgctacagg | 3180 |
| catcgtggtg tcacgctcgt cgtttggtat ggcttcattc agctccggtt cccaacgatc | 3240 |
| aaggcgagtt acatgatccc ccatgttgtg caaaaaagcg gttagctcct tcggtcctcc | 3300 |
| gatcgttgtc agaagtaagt tggccgcagt gttatcactc atggttatgg cagcactgca | 3360 |
| taattctctt actgtcatgc catccgtaag atgcttttct gtgactggtg agtactcaac | 3420 |
| caagtcattc tgagaatagt gtatgcggcg accgagttgc tcttgcccgg cgtcaatacg | 3480 |
| ggataatacc gcgccacata gcagaacttt aaaagtgctc atcattggaa aacgttcttc | 3540 |
| ggggcgaaaa ctctcaagga tcttaccgct gttgagatcc agttcgatgt aacccactcg | 3600 |
| tgcacccaac tgatcttcag catctttac tttcaccagc gtttctgggt gagcaaaaac | 3660 |
| aggaaggcaa aatgccgcaa aaagggaat aaggcgaca cggaaatgtt gaatactcat | 3720 |
| actcttcctt tttcaatatt attgaagcat ttatcagggt tattgtctca tgagcggata | 3780 |
| catatttgaa tgtatttaga aaataaaaca aatagggg t ccgcgcacat ttccccgaaa | 3840 |
| agtgccac | 3848 |

```
<210> SEQ ID NO 5
<211> LENGTH: 291
<212> TYPE: DNA
<213> ORGANISM: Artificial
<220> FEATURE:
<223> OTHER INFORMATION: PCR fragment

<400> SEQUENCE: 5
attcgatcgt ggtctcagaa tcctggtggt gagcaatggt ttcaaccatg taccggatgt      60
gttctgccat gcgctcctga aactcaacat cgtcatcaaa cgcacgggta atggattttt     120
tgctggcccc gtggcgttgc aaatgatcga tgcatagcga ttcaaacagg tgctggggca    180
ggcctttttc catgtcgtct gccagttctg cctctttctc ttcacgggcg agctgctggt    240
agtgacgcgc ccagctctga gcctcaagac gcttggagac cagctagcca t            291

<210> SEQ ID NO 6
<211> LENGTH: 61
<212> TYPE: DNA
<213> ORGANISM: Artificial
<220> FEATURE:
<223> OTHER INFORMATION: PS079 (includes a C12 linker)
<220> FEATURE:
<221> NAME/KEY: misc_binding
<222> LOCATION: (42)..(43)
<223> OTHER INFORMATION: C12 linker

<400> SEQUENCE: 6
gaagagcacc agaaagacca aaagacacac gggaaccgaa cttttcccag tcacgacgtt     60
g                                                                    61

<210> SEQ ID NO 7
<211> LENGTH: 20
<212> TYPE: DNA
<213> ORGANISM: Artificial
<220> FEATURE:
<223> OTHER INFORMATION: PS080
<220> FEATURE:
<221> NAME/KEY: misc_binding
<222> LOCATION: (1)..(1)
<223> OTHER INFORMATION: Biotine

<400> SEQUENCE: 7
ccatgattac gccaagctcg                                                 20

<210> SEQ ID NO 8
<211> LENGTH: 39
<212> TYPE: DNA
<213> ORGANISM: Artificial
<220> FEATURE:
<223> OTHER INFORMATION: PS103

<400> SEQUENCE: 8
attcgatcgt ggtctcagaa tcctggtggt gagcaatgg                            39

<210> SEQ ID NO 9
<211> LENGTH: 41
<212> TYPE: DNA
<213> ORGANISM: Artificial
<220> FEATURE:
<223> OTHER INFORMATION: PS104

<400> SEQUENCE: 9
atggctagct ggtctccaag cgtcttgagg ctcagagctg g                         41

<210> SEQ ID NO 10
```

```
<211> LENGTH: 21
<212> TYPE: DNA
<213> ORGANISM: Artificial
<220> FEATURE:
<223> OTHER INFORMATION: PS101
<220> FEATURE:
<221> NAME/KEY: misc_feature
<222> LOCATION: (1)..(1)
<223> OTHER INFORMATION: 5' phosphorylation

<400> SEQUENCE: 10
gcttgaccat ctaaggttat c                                              21

<210> SEQ ID NO 11
<211> LENGTH: 120
<212> TYPE: DNA
<213> ORGANISM: Artificial
<220> FEATURE:
<223> OTHER INFORMATION: PS070

<400> SEQUENCE: 11
ttggtgaaga aggaagatga ttatattata tatgtgatgg agttgttaag tatagaatga    60
atttattaag aggtattaaa tggtatatgt ggtgtatagg agtgataacc ttagatggtc   120

<210> SEQ ID NO 12
<211> LENGTH: 74
<212> TYPE: DNA
<213> ORGANISM: Artificial
<220> FEATURE:
<223> OTHER INFORMATION: PS102

<400> SEQUENCE: 12
attcgataac cttagatggt caagcatgcc gcttttcggt tcccgtgtgt cttttggtct    60
ttctggtgct cttc                                                     74

<210> SEQ ID NO 13
<211> LENGTH: 53
<212> TYPE: DNA
<213> ORGANISM: Artificial
<220> FEATURE:
<223> OTHER INFORMATION: PS108
<220> FEATURE:
<221> NAME/KEY: misc_feature
<222> LOCATION: (1)..(1)
<223> OTHER INFORMATION: 5' phosphorylation

<400> SEQUENCE: 13
attcgaagag caccagaaag accaaaagac acacgggaac cgaaaagcgg cat           53

<210> SEQ ID NO 14
<211> LENGTH: 40
<212> TYPE: DNA
<213> ORGANISM: Artificial
<220> FEATURE:
<223> OTHER INFORMATION: PS109

<400> SEQUENCE: 14
ttcggttccc gtgtgtcttt tggtctttct ggtgctcttc                          40

<210> SEQ ID NO 15
<211> LENGTH: 33
<212> TYPE: DNA
<213> ORGANISM: Artificial
<220> FEATURE:
<223> OTHER INFORMATION: PS046
<220> FEATURE:
<221> NAME/KEY: misc_feature
```

```
<222> LOCATION: (1)..(1)
<223> OTHER INFORMATION: 5' phosphorylation

<400> SEQUENCE: 15
gcttgccact tgaagatttt ttcttcaagt ggc                              33

<210> SEQ ID NO 16
<211> LENGTH: 67
<212> TYPE: DNA
<213> ORGANISM: Artificial
<220> FEATURE:
<223> OTHER INFORMATION: PS115
<220> FEATURE:
<221> NAME/KEY: misc_feature
<222> LOCATION: (1)..(1)
<223> OTHER INFORMATION: 5' phosphorylation

<400> SEQUENCE: 16
attcgataac cttagatggt caagcagcat gccgcttgtg tgtcttttgg tctttctggt   60
gctcttc                                                             67

<210> SEQ ID NO 17
<211> LENGTH: 45
<212> TYPE: DNA
<213> ORGANISM: Artificial
<220> FEATURE:
<223> OTHER INFORMATION: PS116
<220> FEATURE:
<221> NAME/KEY: misc_feature
<222> LOCATION: (1)..(1)
<223> OTHER INFORMATION: 5' phosphorylation

<400> SEQUENCE: 17
attcgaagag caccagaaag accaaaagac acacaagcgg catcg                  45

<210> SEQ ID NO 18
<211> LENGTH: 40
<212> TYPE: DNA
<213> ORGANISM: Artificial
<220> FEATURE:
<223> OTHER INFORMATION: PS118

<400> SEQUENCE: 18
ttcggttccc gtgtgtcttt tggtctttct ggtgctcttc                        40
```